United States Patent [19]

Kaas et al.

[11] Patent Number: 5,763,611
[45] Date of Patent: Jun. 9, 1998

[54] THIO-SUBSTITUTED CYCLIC PHOSPHONATE COMPOUNDS, PHARMACEUTICAL COMPOSITIONS, AND METHODS FOR TREATING ABNORMAL CALCIUM AND PHOSPHATE METABOLISM

[75] Inventors: Susan Mary Kaas, Sherburne, N.Y.; Frank Hallock Ebetino; Marion David Francis, both of Cincinnati, Ohio

[73] Assignee: The Procter & Gamble Company, Cincinnati, Ohio

[21] Appl. No.: 52,696

[22] Filed: Apr. 30, 1993

Related U.S. Application Data

[63] Continuation-in-part of Ser. No. 890,886, May 29, 1992, abandoned.

[51] Int. Cl.$^6$ .................................................. C07F 9/28
[52] U.S. Cl. .................................................. 546/21; 546/22
[58] Field of Search ............................... 546/23, 21, 22; 514/80, 82, 89

[56] References Cited

U.S. PATENT DOCUMENTS

| | | | |
|---|---|---|---|
| 4,208,401 | 6/1980 | Bauman | 424/54 |
| 4,267,108 | 5/1981 | Blum et al. | 260/326.61 |
| 4,407,761 | 10/1983 | Blum et al. | 260/502.5 C |
| 4,687,768 | 8/1987 | Benedict et al. | 514/102 |
| 4,746,654 | 5/1988 | Breliere et al. | 514/108 |
| 4,784,993 | 11/1988 | Bosies et al. | 514/93 |
| 4,868,164 | 9/1989 | Ebetino et al. | 514/80 |
| 4,876,247 | 10/1989 | Barbier et al. | 514/89 |
| 4,902,695 | 2/1990 | Ornstein | 514/307 |
| 4,922,007 | 5/1990 | Kieczykowski et al. | 562/13 |
| 4,933,472 | 6/1990 | Isomura et al. | 549/218 |
| 4,939,130 | 7/1990 | Jaeggi et al. | 514/94 |
| 4,939,131 | 7/1990 | Benedict et al. | 514/102 |
| 4,971,958 | 11/1990 | Bosies et al. | 514/89 |
| 4,997,821 | 3/1991 | Cordi et al. | 514/82 |
| 5,071,840 | 12/1991 | Ebetino et al. | 514/89 |
| 5,104,863 | 4/1992 | Benedict et al. | 514/80 |
| 5,137,880 | 8/1992 | Ebetino et al. | 514/80 |
| 5,177,240 | 1/1993 | Cordi et al. | 546/23 |

FOREIGN PATENT DOCUMENTS

| | | |
|---|---|---|
| A-26738/88 | 6/1989 | Australia . |
| A-45467/89 | 5/1990 | Australia . |
| 0100718 | 2/1984 | European Pat. Off. . |
| 0170228 | 2/1986 | European Pat. Off. . |
| 0186405 | 7/1986 | European Pat. Off. . |
| 0298553 | 1/1989 | European Pat. Off. . |
| 4011777 | 10/1990 | Germany . |
| WO 90/12017 | 10/1990 | WIPO . |
| WO 91/10646 | 7/1991 | WIPO . |

*Primary Examiner*—Amelia Owens
*Attorney, Agent, or Firm*—Richard A. Hake; Karen F. Clark; Carl J. Roof

[57] ABSTRACT

The present invention relates to thio-substituted cyclic phosphonate compounds including bisphosphonates and phosphonoalkylphosphinates, and the pharmaceutically-acceptable salts and esters thereof. The present invention further relates to pharmaceutical compositions containing a safe and effective amount of a compound of the present invention, and pharmaceutically-acceptable excipients. Finally, the present invention relates to methods for treating or preventing pathological conditions characterized by abnormal calcium and phosphate metabolism in humans or other mammals including treating or preventing osteoporosis and arthritis, especially rheumatoid arthritis and osteoarthritis. The compounds may be monocyclic or bicyclic and have the following general structure:

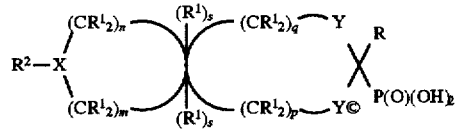

wherein (a) X and Y are independently selected from nil, O, S, and N;

(b) R is $PO_3H_2$ or $P(O)(OH)R^4$, wherein $R^4$ is substituted or unsubstituted $C_1$–$C_8$ alkyl;

(c) m and n are integers from 0 to 5, and m+n equals 0 to 5;

(d) p and q are integers from 0 to 3, and p+q equals 0 to 3;

(e) s is an integer from 0 to 2 and when X is nil and m+n=0, s=2; and (f) $R^1$ and $R^2$ are selected from various substituents; provided that at least one thio substituent is present.

6 Claims, No Drawings

THIO-SUBSTITUTED CYCLIC PHOSPHONATE COMPOUNDS, PHARMACEUTICAL COMPOSITIONS, AND METHODS FOR TREATING ABNORMAL CALCIUM AND PHOSPHATE METABOLISM

This is a CIP of Ser. No. 07/890,886 filed on May 29, 1992, now abandoned.

BACKGROUND OF THE INVENTION

This invention relates to novel thio-substituted cyclic phosphonate compounds, including bisphosphonates, phosphonoalkyl-phosphinates, phosphonocarboxylates, and phosphonosulfonates, preferably bisphosphonates and phosphonoalkylphosphinates. This invention further relates to pharmaceutical compositions containing these novel compounds. This invention also relates to a method of treating or preventing metabolic bone disorders characterized by abnormal calcium and phosphate metabolism by utilizing a compound or pharmaceutical composition of the present invention. Specifically, this invention relates to a method of treating or preventing osteoporosis and arthritis, especially rheumatoid arthritis and osteoarthritis, by utilizing a compound or pharmaceutical composition of the present invention.

A number of pathological conditions which can afflict humans and lower animals involve abnormal calcium and phosphate metabolism. Such conditions may be divided into two broad categories:

(1) Conditions which are characterized by anomalous mobilization of calcium and phosphate leading to general or specific bone loss, such as osteoporosis and Paget's disease; or excessively high calcium and phosphate levels in the fluids of the body, such as hypercalcemia of tumor origin. Such conditions are sometimes referred to herein as pathological hard tissue demineralizations.

(2) Conditions which cause or result from deposition of calcium and phosphate anomalously in the body, such as arthritis. These conditions are sometimes referred to herein as pathological calcifications.

The first category includes the most common metabolic bone disorder, osteoporosis; osteoporosis is a condition in which bone hard tissue is lost disproportionately to the development of new hard tissue. Osteoporosis can be generally defined as the reduction in the quantity of bone, or the atrophy of skeletal tissue. Marrow and bone spaces become larger, fibrous binding decreases, and compact bone becomes fragile. Osteoporosis can be subclassified as menopausal, senile, drug-induced (e.g. adreno-corticoid, as can occur in steroid therapy), disease-induced (arthritic and tumor), etc.; however, the manifestations are the same. In general, there are two types of osteoporosis: primary and secondary. "Secondary osteoporosis" is the result of a separate identifiable disease process or agent. However, approximately 90% of all osteoporosis cases are "primary osteoporosis". Such primary osteoporosis includes postmenopausal osteoporosis, disuse osteoporosis, age-associated osteoporosis (affecting a majority of individuals over the age of 70 to 80), and idiopathic osteoporosis affecting middle-aged and younger men and women.

For some osteoporotic individuals the loss of bone tissue is sufficiently great so as to cause mechanical failure of the bone structure. Bone fractures often occur, for example, in the hip and spine of women suffering from postmenopausal osteoporosis. Kyphosis (abnormally increased curvature of the thoracic spine) may also result.

The mechanism of bone loss in osteoporotics is believed to involve an imbalance in the process of "bone remodeling". Bone remodeling occurs throughout life, renewing the skeleton and maintaining the strength of bone. This remodeling involves the erosion and filling of discrete sites on the surface of bones, by an organized group of cells called "basic multicellular units" or "BMUs". BMUs primarily consist of "osteoclasts", "osteoblasts", and their cellular precursors. In the remodeling cycle, bone is resorbed at the site of an "activated" BMU by an osteoclast, forming a resorption cavity. This cavity is then filled with bone by an osteoblast.

Normally, in adults, the remodeling cycle results in a small deficit in bone, due to incomplete filling of the resorption cavity. Thus, even in healthy adults, age-related bone loss occurs. However, in osteoporotics, there may be an increase in the number of BMUs that are activated. This increased activation accelerates bone remodeling, resulting in abnormally high bone loss.

Although its etiology is not fully understood, there are many risk factors thought to be associated with osteoporosis. These include low body weight, low calcium intake, physical inactivity, and estrogen deficiency.

Current osteoporosis treatment consists primarily of calcium and estrogen administration.

The second category, involving conditions manifested by anomalous calcium and phosphate deposition, includes myositis ossificans progressive, calcinosis universalis, and such afflictions as arthritis (including, for example, rheumatoid arthritis and osteoarthritis), neuritis, bursitis, tendonitis, and other conditions which predispose involved tissue to deposition of calcium.

In addition to osteoporosis, bone loss can result from rheumatoid arthritis and osteoarthritis. Rheumatoid arthritis is a chronic, systemic and articular inflammatory disorder characterized by weakening of the joint capsules and ligaments, followed by destruction of cartilage, ligaments, tendon and bone, and a decrease in viscosity and other alterations in the synovial fluid. Rheumatoid arthritis symptoms include systemic weakness, fatigue, localized pain, stiffness and weakness and swelling and deformation of the joints of the body. Rheumatoid arthritis is most common in women in the fourth to sixth decade of life.

The pathogenesis of rheumatoid arthritis, leading to the destruction of the joints, is characterized by two phases: 1) an exudative phase involving the microcirculation and the synovial cells that allow an influx of plasma proteins and cellular elements into the joint and 2) a chronic inflammatory phase occurring in the sub-synovium and sub-chondral bone, characterized by pannus granulation tissue) formation in the joint space, bone erosion, and cartilage destruction. The pannus may form adhesions and scar tissue which causes the joint deformities characteristic of rheumatoid arthritis.

The etiology of rheumatoid arthritis remains obscure. Infectious agents such as bacteria and viruses have been implicated. A current hypothesis is that the Epstein-Barr (EBV) virus is a causative agent for rheumatoid Arthritis.

Current rheumatoid arthritis treatment consists predominantly of symptomatic relief by administration of non-steroidal anti-inflammatory drugs. Non-steroidal anti-inflammatory drug treatment is mainly effective in the early stages of rheumatoid arthritis; it is unlikely it will produce suppression of joint inflammation if the disease is present for more than one year. Gold, methotrexate, immunosuppressants and corticosteroids have been tried with limited success.

On the other hand, osteoarthritis is an inherently non-inflammatory disorder of the movable joints characterized by deterioration and abrasion of articular cartilage, as well as by formation of new bone at the joint surface. As osteoarthritis progresses, the surface of the articular cartilage is disrupted and wear particles gain access to the synovial fluid which in turn stimulates phagocytosis by macrophage cells. Thus, an inflammatory response is eventually induced in osteoarthritis. Common clinical symptoms of osteoarthritis include cartilaginous and bony enlargements of the finger joints and stiffness on awakening, and pain from movement.

Common symptomatic treatments for osteoarthritis include analgesics, anti-inflammatories, steroids, and physical therapy.

A variety of phosphonic acid derivatives have been proposed for use in the treatment and prophylaxis of diseases involving abnormal calcium and phosphate metabolism. For example, numerous references, all incorporated by reference herein, disclose compositions containing polyphosphonates, in particular bisphosphonates such as ethane-1-hydroxy-1,1-diphosphonic acid ("EHDP"), and their use in inhibiting anomalous deposition and mobilization of calcium and phosphate in animal tissue: U.S. Pat. No. 3,683,080, issued Aug. 8, 1972 and U.S. Pat. No. 4,230,700, issued Oct. 28, 1980, both to Francis, and U.S. Pat. No. 4,868,164 to Ebetino, issued Sep. 19, 1989. Numerous other references describe heterocyclic-substituted diphosphonic acids useful for the treatment of osteoporosis and/or arthritis, and are hereby incorporated by reference herein: U.S. Pat. No. 4,868,164, to Ebetino, et al., issued Sep. 19, 1989; U.S. Pat. No. 5,104,863, to Benedict, et al., issued Apr. 14, 1992; U.S. Pat. No. 4,267,108, to Blum et al., issued May 12, 1981; European Patent Application Publication of Boehringer Mannheim GmbH No. 170,228, published Feb. 5, 1986; European Patent Application Publication No. 186,405, of Benedict and Perkins, published Jul. 2, 1986; U.S. Pat. No. 4,754,993, Bosies, et al. issued Nov. 15, 1988; U.S. Pat. No. 4,939,130, Jaeggi, et al., issued Jul. 3, 1990; U.S. Pat. No. 4,971,958, Bosies, et al. issued Nov. 20, 1990; DE 40 11 777, Jaeggi, K., published Oct. 18, 1990; WO 90/12017, of Dunn, et al., published Oct. 18, 1990; WO 91/10646, Youssefyeh, R., et al., published Jul. 25, 1991; AU-A-26738/88, Jaeggi, published Jun. 15, 1989, AU-A-45467/89 (assigned to Ciba-Geigy), published May 31, 1990; and U.S. Pat. No. 4,208,401 to Bauman issued Jun. 17, 1980.

In addition, several references describe sulfur containing phosphonic acids which are said to be useful in the treatment of inflammation symptoms. See e.g. U.S. Pat. No. 4,746,654 to Breliere et al. (assigned to Sanofi), issued May 24, 1988; U.S. Pat. No. 4,876,247 to Barbier et al., issued Oct. 24, 1989; and EPO 100,718 to Breliere et al. (assigned to Sanofi), published Feb. 15, 1984. Also, U.S. Pat. No. 5,071,840 to Ebetino et al., issued Dec. 10, 1991, discloses sulfur-containing heterocycle-substituted diphosphonates in which the diphosphonate-substituted carbon moiety is attached, via a sulfur-containing linking chain, to a carbon atom in a nitrogen-containing six-membered ring heterocycle. The compounds described therein are useful in the treatment of conditions involving abnormal calcium and phosphate metabolism, specifically osteoporosis and arthritis.

Further, European Patent 0,298,553 to Ebetino published Jan. 11, 1989 describes thiol-substituents amongst a myriad of other substituents, suitable as substituents on methylene phosphonoalkylphosphinic acids. There is no teaching therein, however, that a thiol substituent increases the antiresorptive and antiarthritic activity of methylene phosphonoalkylphosphinic acids over the numerous other substituents disclosed.

None of these references, however, disclose the utility of thio-substituted monocyclic or bicyclic bisphosphonates, phosphonocarboxylates, and phosphonosulfonates in preventing and treating any of osteoporosis, rheumatoid arthritis, or osteoarthritis. Further, the compounds of the present invention have osteoprotective activity. The term "osteoprotective activity" as used herein means disease-modifying activity on bone and surrounding soft tissue at the site of joint destruction in arthritic conditions. Osteoprotective activity is an additional benefit in the treatment of arthritis, over and above merely relieving the symptoms of inflammation. The thio-substituents defined herein include thiol, thioesters, alkyl thioesters, thiocarbamates, alkyl thiocarbamates, dithiocarbamates, alkyl dithiocarbamates, thiocarbonates, alkyl thiocarbonates, dithiocarbonates, and alkyl dithiocarbonates.

It has been surprisingly discovered that the thio-substituted cyclic phosphonate compounds of the present invention have more potent bone antiresorptive activity, and therapeutic utility in treating osteoporosis and arthritis, than cyclic phosphonate compounds that are not thio-substituted. It is therefore an object of the present invention to provide new more potent compounds which are potent bone resorption inhibiting agents useful in osteoporosis therapy and anti-arthritic agents useful in the treatment of arthritis, especially osteoarthritis and rheumatoid arthritis. It is a further object of the present invention to provide pharmaceutical compositions useful for the treatment and prophylaxis of abnormal calcium and phosphate metabolism and for the treatment and prophylaxis of arthritis, especially rheumatoid arthritis and osteoarthritis. In addition, it is an object of the present invention to provide methods for treating or preventing diseases characterized by abnormal calcium and phosphate metabolism in humans or other mammals, including osteoporosis and arthritis, especially rheumatoid arthritis and osteoarthritis.

These and other objects of the present invention will become apparent from the detailed disclosure of the present invention provided hereinafter.

SUMMARY OF THE INVENTION

The present invention relates to thio-substituted monocyclic and bicyclic phosphonate compounds including bisphosphonates, phosphonoalkylphosphinates, phosphonocarboxylates, and phosphonosulfonates, and the pharmaceutically-acceptable salts and esters thereof. Preferred compounds disclosed herein are bisphosphonates and phosphonoalkylphosphinates. The present invention further relates to pharmaceutical compositions containing a safe and effective amount of a compound of the present invention, and pharmaceutically-acceptable excipients. Finally, the present invention relates to methods for treating or preventing pathological conditions characterized by abnormal calcium and phosphate metabolism in humans or other mammals including treating or preventing osteoporosis and arthritis, especially rheumatoid arthritis and osteoarthritis. This method comprises administering to a human or other mammal in need of such treatment of a safe and effective amount of a compound or composition of the present invention. These compounds have the following general structure:

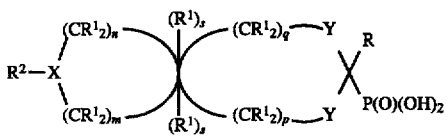

wherein (a) X and Y are independently selected from nil, O, S, and N;

(b) R is COOH, $SO_3H$, $PO_3H_2$, $P(O)(OH)R^4$, wherein $R^4$ is substituted or unsubstituted $C_1-C_8$ alkyl;

(c) m and n are integers from 0 to 5, and m+n equals 0 to 5;

(d) p and q are integers from 0 to 3, and p+q equals 0 to 3;

(e) s is the integer 0 to 2 and when m+n=0 and X is nil, s is 2;

(f) each $R^1$ is independently selected from —$SR^6$; $R^8SR^6$; nil; hydrogen; unsubstituted or substituted $C_1-C_8$ alkyl; unsubstituted or substituted aryl; hydroxy; —$CO_2R^3$; —$O_2CR^3$; —$NR^3_2$; —$OR^3$; —$C(O)N(R^3)_2$; —$N(R^3)C(O)R^3$; substituted or unsubstituted benzyl; nitro; and combinations thereof;

(g) $R^2$ is one or more substituents of X and Y and is independently selected from the group consisting of $R^8SR^6$; nil; hydrogen; unsubstituted or substituted $C_1-C_8$ alkyl; unsubstituted or substituted aryl; —$CO_2R^3$; —$C(O)N(R^3)_2$; substituted or unsubstituted benzyl; or combinations thereof;

(h) $R^3$ is independently selected from hydrogen; substituted or unsubstituted $C_1-C_8$ alkyl; or $R^8SR^6$;

(i) $R^6$ is independently selected from H; $C(O)R^7$; —$C(S)R^7$; $C(O)N(R^7)_2$; $C(S)N(R^7)_2$, $C(O)OR^7$; and $C(S)OR^7$; wherein $R^7$ is hydrogen, or substituted or unsubstituted $C_1-C_8$ alkyl; and (j) $R^8$ is substituted or unsubstituted $C_1-C_8$ alkyl; provided that at least one of $R^1$, $R^2$, and $R^3$ is $SR^6$ or $R^8SR^6$.

As stated above, it is essential that at least one of $R^1$, $R^2$, and $R^3$ is $SR^6$ or $R^8SR^6$. When either of $R^1$, or $R^2$ is $SR^6$, the substituents in the compounds of the present invention are thiols, thioesters, dithioesters, thiocarbamates, dithiocarbamates, thiocarbonates, and dithiocarbonates. When any of $R^1$, $R^2$, or $R^3$ is $R^8SR^6$, the substituents in the compounds of the present invention are alkyl thiols, alkyl thioesters, alkyl dithioesters, alkyl thiocarbamates, alkyl dithiocarbamates, alkyl thiocarbonates and alkyl dithiocarbonates.

The present invention further relates to pharmaceutical compositions containing a safe and effective amount of a compound of the present invention, and pharmaceutically-acceptable excipients. Finally, the present invention relates to methods for treating or preventing pathological conditions characterized by abnormal calcium and phosphate metabolism in humans or other mammals. This method comprises administering to a human or other mammal in need of such treatment a safe and effective amount of a compound or composition of the present invention.

Definitions and Usage of Terms

The following is a list of definitions for terms used herein.

"Heteroatom" is a nitrogen, sulfur, or oxygen atom. Groups containing one or more heteroatoms may contain different heteroatoms.

"Alkyl" is a saturated or unsaturated, unsubstituted or substituted, straight-chain or branched, hydrocarbon chain having 1 to 8 carbon atoms, and preferably, unless otherwise stated, from 1 to 4 carbon atoms. The term "Alkyl" therefore includes alkenyls having from 2 to 8 carbons, preferably from 2 to 4 carbons, having at least one olefinic double bond, as well as alkynls having from 2 to 8 carbons, preferably from 2 to 4 carbons, having at least one triple bond. Preferred alkyl groups include, but are not limited to, methyl, ethyl, propyl, isopropyl, and butyl.

"Heteroalkyl" is an unsubstituted or substituted, saturated or unsaturated chain having from 3 to 8-members and comprising carbon atoms and one or two heteroatoms.

"Carbocyclic ring" or "Carbocycle" as used herein is an unsubstituted or substituted, saturated, unsaturated or aromatic, hydrocarbon ring, generally containing from 3 to 8 atoms, preferably 5 to 7 atoms. Carbocyclic rings may be monocyclic, having from 3 to 8, preferably 5 to 7, carbon atoms, or polycyclic. Polycyclic carbocycles consisting of two rings generally have 6 to 16, preferably 10 to 12, atoms, while polycyclic carbocycles having three rings generally contain 3 to 17, preferably 14 to 15, atoms. Using the formulae provided herein, in a monocyclic carbocycle X is nil, m+n=0, s=2, and Y is nil. In a polycyclic carbocycle X is nil, m+n=1–3, s=0–2 and Y is nil.

"Heterocyclic ring" or "Heterocycle" as used herein is an unsubstituted or substituted, saturated, unsaturated or aromatic ring comprised of carbon atoms and one or more heteroatoms in the ring. The term "heterocyclic ring moieties" as used herein comprises monocyclic or polycyclic ring systems, fused or unfused, saturated or unsaturated, substituted or unsubstituted. Unless otherwise stated the heteroatoms may be independently chosen from nitrogen, sulfur, and oxygen. Heterocyclic rings may be monocyclic or polycyclic. Monocyclic rings generally contain from 3 to 8 atoms, preferably from 5 to 7 atoms. Polycyclic ring systems consisting of two rings generally contain from 6 to 16, preferably from 10 to 12 atoms. Polycyclic ring systems consisting of three rings generally contain from 13 to 17 atoms, preferably from 14 to 15 atoms. In addition, a polycyclic heterocyclic ring moiety may consist solely of heterocycles, or of both heterocycles, or carbocycles. Each heterocyclic ring moiety must have at least one nitrogen atom. The other heteroatoms may be chosen from oxygen, nitrogen, or sulfur. Using the formula provided herein, in a monocyclic heterocycle, X is nil, m+n=0, s=2 and Y is O, S, or N. In a polycyclic heterocycle, X is nil, O, S, or N; m+n=1–3, s=0–2 and Y is nil, O, S, or N.

"Aryl" is an aromatic carbocyclic ring. Preferred aryl groups include, but are not limited to, phenyl, tolyl, xylyl, cumenyl, and naphthyl.

"Heteroaryl" is an aromatic heterocyclic ring. Preferred heteroaryl groups include, but are not limited to, thienyl, furyl, pyrrolyl, pyridinyl, pyrazinyl, oxazolyl, thiazolyl, quinolinyl, pyrimidinyl, and tetrazolyl.

"Alkoxy" is an oxygen atom having a hydrocarbon chain substituent, where the hydrocarbon chain is an alkyl or alkenyl (e.g., —O-alkyl or —O-alkenyl). Preferred alkoxy groups include, but are not limited to, methoxy, ethoxy, propoxy, and alkyloxy.

"Hydroxyalkyl" is a substituted hydrocarbon chain which has a hydroxy substituent (e.g., —OH), and may have other substituents. Preferred hydroxyalkyl groups include, but are not limited to, hydroxyethyl, hydroxypropyl, and hydroxyalkyl.

"Carboxyalkyl" is a substituted hydrocarbon chain which has a carboxy substituent (e.g. —COOH) and may have other substituents. Preferred carboxyalkyl groups include carboxymethyl, carboxyethyl, and their acids and esters.

"Aminoalkyl" is a hydrocarbon chain (e.g. alkyl) substituted with an amine moiety (e.g., NH-alkyl-), such as aminomethylene.

"Alkylamino" is an amino moiety having one or two alkyl substituents (e.g., —N-alkyl), such as dimethylamine.

"Alkenylamino" is an amino moiety having one or two alkenyl substituents (e.g., —N-alkenyl).

"Alkynalamino" is an amino moiety having one or two alkynyl substituents (e.g., —N-alkynyl).

"Alkylimino" is an imino moiety having one or two alkyl substituents (e.g., —N-alkyl-).

"Arylalkyl" is an alkyl moiety substituted with an aryl group. Preferred arylalkyl groups include benzyl and phenylethyl.

"Arylamino" is an amine moiety substituted with an aryl group (e.g., —NH-aryl).

"Aryloxy" is an oxygen atom having an aryl substituent (e.g., —O-aryl).

"Acyl" or "carbonyl" is a carbon to oxygen double bond (e.g., R—C(=O)—). Preferred alkylacyl groups include, but are not limited to, acetyl, propionyl, butanoyl, and benzoyl.

"Acyloxy" is an oxygen atom having an acyl substituent (e.g., —O-acyl); for example, —O-C(=O)-alkyl.

"Acylamino" is an amino moiety having an acyl substituent (e.g., —N-acyl); for example, —NH-(C=O)-alkyl.

"Halo", "halogen", or "halide" is a chloro, bromo, fluoro, or iodo atom radical. Chloro, bromo, and fluoro are preferred halides.

Also, as referred to herein, a "lower" hydrocarbon moiety (e.g., "lower" alkyl) is a hydrocarbon chain comprised of from, unless otherwise stated, 1 to 6, preferably from 1 to 4, carbon atoms.

As used herein, the term "thio-substituent" is depicted by $SR^6$ or $R^8SR^6$, wherein $R^8$ is a $C_1$-$C_8$ alkyl. Particular thio-substituents include thiol (—SH, where $R^6$=H); thioesters

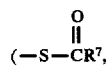

where $R^6$=C(O)$R^7$); dithioesters

where $R^6$ is C(S)$R^7$); thiocarbamates

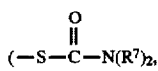

where $R^6$ is C(O)N($R^7$)$_2$; dithiocarbamates

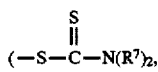

where $R^6$ is C(S)N($R^7$)$_2$; thiocarbonates

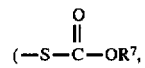

where $R^6$ is C(O)O$R^7$), and dithiocarbonates

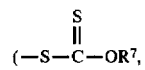

where $R^6$ is C(S)O$R^7$). $R^7$ as used herein is hydrogen or substituted or unsubstituted $C_1$-$C_8$ alkyl. It is to be understood that when the $SR^6$ groups defined above can be preceded by an $R^8$ (a $C_1$-$C_8$ alkyl), the thio-substituent group is $R^8SR^6$; this would yield alkyl thiols, alkyl thioesters, alkyl dithioesters, alkyl thiocarbamates, alkyl dithiocarbamates, alkyl thiocarbonates and alkyl dithiocarbonates.

The terms "bisphosphonate" or "bisphosphonic acid" as used herein relate to those phosphonate or phosphonic acids that have two phosphonate groups attached to the same carbon and are used interchangeably with the terms diphosphonate and diphosphonic acid. Using the structures described herein, in these compounds, the moiety R is $PO_3H_2$.

A "pharmaceutically-acceptable" salt is a cationic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987, hereby incorporated by reference herein. Preferred cationic salts include the alkali-metal salts (such as sodium and potassium), and alkaline earth metal salts (such as magnesium and calcium). Preferred anionic salts include the halide (such as chloride), acetate and phosphate salts.

A "biohydrolyzable ester" is an ester of the thio-substituted phosphate compounds that does not interfere with the activity of the compounds, or that is readily metabolized by a human or other mammal to yield an active phosphonate compound. Many such esters are known in the art, as described in World Patent Publication 87/05297, Johnston et al., published Sep. 11, 1987, and hereby incorporated by reference herein. Such esters include lower alkyl esters, lower acyloxyalkyl esters (such as acetoxylmethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters, and acylamino alkyl esters (such as acetamidomethyl esters).

As defined above and as used herein, substituent groups may themselves be substituted. Such substitution may be with one or more substituents. Such substituents include, but are not limited to, those listed in C. Hansch and A. Leo, *Substituent Constants for Correlation Analysis in Chemistry and Biology* (1979), hereby incorporated by reference herein. Preferred substituents include, but are not limited to, alkyl, alkenyl, alkoxy, hydroxy, oxo, amino, aminoalkyl (e.g. aminomethyl, etc.), cyano, halo, carboxy, alkoxyacetyl (e.g. carboethoxy, etc.), thio, thiol, aryl, cycloalkyl, heteroaryl, heterocycloalkyl (e.g., piperidinyl, morpholinyl, piperazinyl, pyrrolidinyl, etc.), imino, thioxo, hydroxyalkyl, aryloxy, arylalkyl, and combinations thereof.

DETAILED DESCRIPTION OF THE INVENTION

Thio-substituted cyclic ring-containing phosphonate compounds

The compounds of the present invention fall within the class of thio-substituted, monocyclic or bicyclic ring-containing phosphonate compounds which are geminally disubstituted with two phosphonic acids, one phosphonic acid and one phosphinate, one phosphonic acid and one sulfonate, or one phosphonic acid and one carboxylate. It is preferable that the phosphonate compounds are geminally disubstituted with two phosphonic acids or with one phosphonic acid and with one phosphinate. The phosphorus-containing carbon is part of a cyclic ring structure, which has the following general structure:

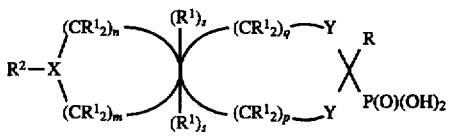

wherein (a) X and Y are independently selected from nil, oxygen, sulfur, or nitrogen;

(b) R is COOH, $SO_3H$, $PO_3H_2$, $P(O)(OH)R^4$, wherein $R^4$ is substituted or unsubstituted $C_1$-$C_8$ alkyl;

(c) m and n are integers from 0 to 5, and m+n equals 0 to 5;

(d) p and q are integers from 0 to 3, and p+q equals 0 to 3;

(e) s is an integer from 0 to 2 and when m+n=0 and X is nil, s=2;

(f) each $R^1$ is independently selected from —$SR^6$; —$R^8SR^6$; nil; hydrogen; unsubstituted or substituted $C_1$-$C_8$ alkyl; unsubstituted or substituted aryl; hydroxy; —$CO_2R^3$; —$O_{CR}^3$; —$NR^3_2$; —$N(R^3)C(O)R^3$; —$OR^3$; —$C(O)N(R^3)_2$; substituted or unsubstituted benzyl; nitro; and combinations thereof;

(g) $R^2$ is one or more substituents of X and Y and is independently selected from the group consisting of —$R^8SR^6$; nil; hydrogen; unsubstituted or substituted $C_1$-$C_8$ alkyl; unsubstituted or substituted aryl; —$CO_2R^3$; —$C(O)N(R^3)_2$; substituted or unsubstituted benzyl; or combinations thereof;

(h) $R^3$ is independently selected from hydrogen; substituted or unsubstituted $C_1$-$C_8$ alkyl; or $R^8SR^6$;

(i) $R^6$ is H; —$C(O)R^7$; —$C(S)R^7$; $C(O)N(R^7)_2$; $C(S)N(R^7)_2$, $C(O)OR^7$ or $C(S)OR^7$, wherein $R^7$ is hydrogen, or substituted or unsubstituted $C_1$-$C_8$ alkyl;

(j) $R^8$ is substituted or unsubstituted $C_1$-$C_8$ alkyl; provided that at least one of $R^1$, $R^2$, and $R^3$ is $SR^6$ or $R^8SR^6$.

The $R^1$ moieties are substituents and are independently selected from thio-substituents $SR^6$ or $R^8SR^6$ (including thiol, thioesters, dithioesters, thiocarbamate, dithiocarbamate, thiocarbonate, dithiocarbonate, alkyl thiols, alkyl thioesters, alkyl dithioesters, alkyl thiocarbamates, alkyl dithiocarbamates, alkyl thiocarbonates, and alkyl dithiocarbonates); nil; hydrogen; halogen; substituted or unsubstituted $C_1$-$C_8$ alkyl; unsubstituted or substituted aryl; unsubstituted or substituted benzyl; hydroxy; —$OR^3$; —$C(O)NR^3_2$; —$CO_2R^3$; —$O_2CR^3$; $NR^3_2$; $N(R^3)C(O)R^3$; nitro; and combinations thereof; wherein $R^3$ is independently selected from hydrogen, $R^8SR^6$ or substituted or unsubstituted $C_1$-$C_8$ alkyl, preferably hydrogen. When any $R^1$ is nil, an adjacent $R^1$ must be nil; this indicates an unsaturated chain.

Preferred $R^1$ is $SR^6$, $R^8SR^6$, hydrogen, $C_1$-$C_8$ alkyl, —$NR^3_2$, and hydroxy; and preferred $R^2$ is $R^8SR^6$, hydrogen, and $C_1$-$C_8$ alkyl. More preferred $R^1$ is $SR^6$, $R^8SR^6$, hydrogen, methyl, ethyl, —$NH_2$, and hydroxy; and most preferred $R^1$ is $SR^6$, hydrogen. More preferred $R^2$ is $R^8SR^6$, hydrogen, methyl, and ethyl; and most preferred $R^2$ is hydrogen.

In bicyclic phosphonate compounds, the X-containing moiety may be a 3-, 4-, 5-, or 8-membered ring bound to the Y-containing ring. X may be oxygen, sulfur, nitrogen or nil and may be substituted with $R^2$ or unsubstituted. In monocyclic phosphonate compounds, X is nil, m+n=0, and s=2.

In both the monocyclic phosphonate compounds and the polycyclic phosphonate compounds, the Y-containing moiety is a 3-, 4-, 5-, 6-, 7- or 8 membered ring wherein each Y is independently selected from oxygen, sulfur, nitrogen, or nil and may be substituted with $R^2$ or unsubstituted.

It is imperative that either at least one of $R^1$, $R^2$, or $R^3$ be $SR^6$ or $R^8SR^6$. When any of $R^1$, $R^2$, or $R^3$ is $SR^6$ or $R^8SR^6$, the bicyclic phosphonate compound is thio-substituted. Suitable thio-substituents for the compounds of the present invention include thiol, thioesters, alkyl thioesters, dithioesters, alkyl dithioesters, thiocarbamate, alkyl thiocarbamates, dithiocarbamate, alkyl dithiocarbamates, thiocarbonate, alkyl thiocarbonates, dithiocarbonate and alkyl dithiocarbonates; $R^6$, accordingly, denotes a substituent on the sulfur-containing substituent, —$SR^6$. $R^6$ is hydrogen; —$C(O)R^7$; —$C(S)R^7$; —$C(O)NR^7_2$; —$C(S)NR^7_2$; —$C(O)(OR^7)$; $C(S)(OR^7)$; wherein $R^7$ is hydrogen, or unsubstituted or substituted $C_1$-$C_8$ alkyl. Preferred $R^6$ is H, $C(O)R^7$, $C(O)NR^7_2$; most preferred $R^6$ is H and $C(O)R^7$. Preferred $R^7$ is methyl and ethyl; most preferred $R^7$ is $CH_3$. $R^8$ is substituted or unsubstituted $C_1$-$C_8$ alkyl.

Preferred compounds of the present invention are thio substituted octahydro pyrindine diphosphonic acids, and the pharmaceutically-acceptable salts and esters thereof, having the general structures:

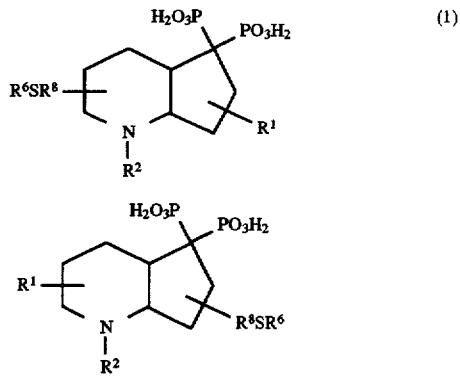

referred to herein as "thio-substituted octahydro-1-pyrindine-5,5-diphosphonic acids";

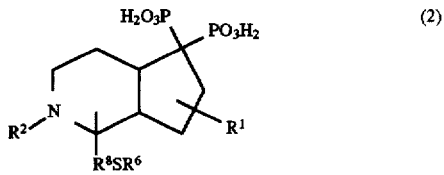

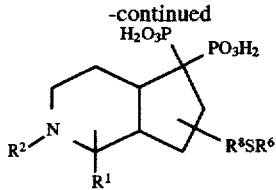

referred to herein as "thio-substituted octahydro-2-pyrindine-5,5-diphosphonic acids";

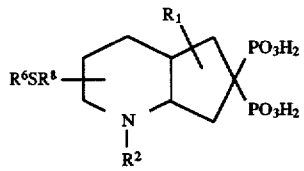

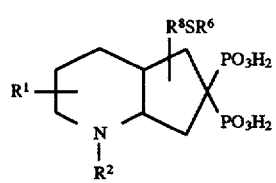

referred to herein as "thio-substituted octahydro-1-pyrindine-6,6-diphosphonic acids";

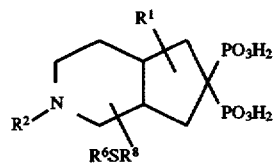

referred to herein as "thio-substituted octahydro-2-pyrindine-6,6-diphosphonic acids";

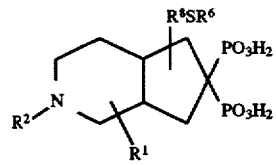

referred to herein as "thio-substituted octahydro-1-pyrindine-7,7-diphosphonic acids";

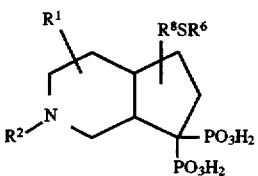

referred to herein as "thio-substituted octahydro-2-pyrindine-7,7-diphosphonic acids";

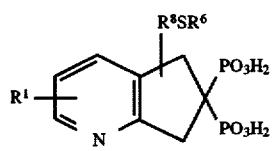

referred to herein as "dihydro-1-pyrindine-6,6-diphosphonic acid";

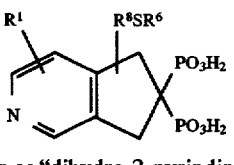

referred to herein as "dihydro-2-pyrindine-6,6-diphosphonic acid"; and

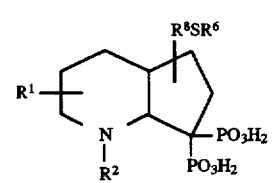

referred to herein as "thio-substituted cyclopentane-1,1-diphosphonic acid".

More preferred compounds of the present invention are substituted or unsubstituted octahydro-1-pyrindine-6,6-diphosphonic acids, and the pharmaceutically-acceptable salts and esters thereof; and substituted or unsubstituted octahydro-2-pyrindine-6,6-diphosphonic acids, and the pharmaceutically-acceptable salts and esters thereof. Most preferred compounds of the present invention are substituted or unsubstituted octahydro-1-pyrindine-6,6-diphosphonic acids, and the pharmaceutically-acceptable salts and esters thereof.

Specific examples of compounds of the present invention include:

octahydro-2-mercapto-1-pyrindine-5,5-bisphosphonic acid;

octahydro-3-mercapto-1-pyrindine-5,5-bisphosphonic acid;

octahydro-4-mercapto-1-pyrindine-5,5-bisphosphonic acid;

octahydro-3-thiomethyl-1-pyrindine-5,5-bisphosphonic acid;

octahydro-3-thioethyl-1-pyrindine-5,5-bisphosphonic acid;

octahydro-7-(2-mercaptoethyl)-1-pyrindine-6,6-bisphosphonic acid;

octahydro-3-thiopropyl-1-pyrindine-5,5-bisphosphonic acid;
octahydro-3-thiobutyl-1-pyrindine-5,5-bisphosphonic acid;
octahydro-2-thioethyl-1-pyrindine-5,5-bisphosphonic acid;
octahydro-4-thiopropyl-1-pyrindine-5,5-bisphosphonic acid;
octahydro-2-methoxy-4-thiobutyl-1-pyrindine-5,5-bisphosphonic acid;
octahydro-2-mercapto-1-pyrindine-6,6-bisphosphonic acid;
octahydro-3-mercapto-1-pyrindine-6,6-bisphosphonic acid;
octahydro-4-mercapto-1-pyrindine-6,6-bisphosphonic acid;
octahydro-3-thiomethyl-1-pyrindine-6,6-bisphosphonic acid;
octahydro-3-thioethyl-1-pyrindine-6,6-bisphosphonic acid;
octahydro-3-thiopropyl-1-pyrindine-6,6-bisphosphonic acid;
octahydro-3-thiobutyl-1-pyrindine-6,6-bisphosphonic acid;
octahydro-2-thioethyl-1-pyrindine-6,6-bisphosphonic acid;
octahydro-4-thiopropyl-1-pyrindine-6,6-bisphosphonic acid;
octahydro-2-methoxy-4-thiobutyl-1-pyrindine-6,6-bisphosphonic acid;
octahydro-2-mercapto-1-pyrindine-7,7-bisphosphonic acid;
octahydro-3-mercapto-1-pyrindine-7,7-bisphosphonic acid;
octahydro-4-mercapto-1-pyrindine-7,7-bisphosphonic acid;
octahydro-3-thiomethyl-1-pyrindine-7,7-bisphosphonic acid;
octahydro-3-thioethyl-1-pyrindine-7,7-bisphosphonic acid;
octahydro-3-thiopropyl-1-pyrindine-7,7-bisphosphonic acid;
octahydro-3-thiobutyl-1-pyrindine-7,7-bisphosphonic acid;
octahydro-2-thioethyl-1-pyrindine-7,7-bisphosphonic acid;
octahydro-4-thiopropyl-1-pyrindine-7,7-bisphosphonic acid;
octahydro-2-methoxy-4-thiobutyl-1-pyrindine-7,7-bisphosphonic acid;
octahydro-1-mercapto-2-pyrindine-5,5-bisphosphonic acid;
octahydro-3-mercapto-2-pyrindine-5,5-bisphosphonic acid;
octahydro-4-mercapto-2-pyrindine-5,5-bisphosphonic acid;
octahydro-4-thiomethyl-2-pyrindine-5,5-bisphosphonic acid;
octahydro-4-thioethyl-2-pyrindine-5,5-bisphosphonic acid;
octahydro-4-thiopropyl-2-pyrindine-5,5-bisphosphonic acid;
octahydro-4-thiobutyl-2-pyrindine-5,5-bisphosphonic acid;
octahydro-3-thioethyl-2-pyrindine-5,5-bisphosphonic acid;
octahydro-1-thiopropyl-2-pyrindine-5,5-bisphosphonic acid;
octahydro-1-methoxy-4-thiobutyl-2-pyrindine-5,5-bisphosphonic acid;
octahydro-4-amino-1-thiobutyl-2-pyrindine-5,5-bisphosphonic acid;
octahydro-4-hydroxy-4-thiobutyl-2-pyrindine-5,5-bisphosphonic acid;
octahydro-1-mercapto-2-pyrindine-6,6-bisphosphonic acid;
octahydro-3-mercapto-2-pyrindine-6,6-bisphosphonic acid;
octahydro-4-mercapto-2-pyrindine-6,6-bisphosphonic acid;
octahydro-4-thiomethyl-2-pyrindine-6,6-bisphosphonic acid;
octahydro-4-thioethyl-2-pyrindine-6,6-bisphosphonic acid;
octahydro-4-thiopropyl-2-pyrindine-6,6-bisphosphonic acid;
octahydro-4-thiobutyl-2-pyrindine-6,6-bisphosphonic acid;
octahydro-3-thioethyl-2-pyrindine-6,6-bisphosphonic acid;
octahydro-1-thiopropyl-2-pyrindine-6,6-bisphosphonic acid;
octahydro-1-methoxy-4-thiobutyl-2-pyrindine-6,6-bisphosphonic acid;
octahydro-4-amino-1-thiobutyl-2-pyrindine-6,6-bisphosphonic acid;
octahydro-4-hydroxy-4-thiobutyl-2-pyrindine-6,6-bisphosphonic acid;
octahydro-1-mercapto-2-pyrindine-7,7-bisphosphonic acid;
octahydro-3-mercapto-2-pyrindine-7,7-bisphosphonic acid;
octahydro-4-mercapto-2-pyrindine-7,7-bisphosphonic acid;
octahydro-4-thiomethyl-2-pyrindine-7,7-bisphosphonic acid;
octahydro-4-thiooctahydro-3-amino-5-(1-mercapto-1-methyl)ethyl-1-pyrindine-octahydro-7-mercapto-1-pyrindine-6,6-bisphosphonic acid;
octahydro-5-(2-thioethyl)-1-pyrindine-6,6-bisphosphonic acid;
octahydro-7-thiomethyl-1-pyrindine-6,6-bisphosphonic acid;
octahydro-7-thiobutyl-1-pyrindine-6,6-bisphosphonic acid;
octahydro-3-amino-7-mercapto-1-pyrindine-6,6-bisphosphonic acid;
octahydro-3-amino-5-thiopropyl-1-pyrindine-6,6-bisphosphonic acid;
octahydro-3-methoxy-7-(1-mercapto-1-methyl)ethyl-1-pyrindine-6,6-bisphosphonic acid;
octahydro-3-amino-5-(1-mercapto-1-methyl)ethyl-1-pyrindine-6,6-bisphosphonic acid;
octahydro-4-thiopropyl-2-pyrindine-7,7-bisphosphonic acid;

octahydro-4-thiobutyl-2-pyrindine-7,7-bisphosphonic acid;
octahydro-3-thioethyl-2-pyrindine-7,7-bisphosphonic acid;
octahydro-1-thiopropyl-2-pyrindine-7,7-bisphosphonic acid;
octahydro-1-methoxy-4-thiobutyl-2-pyrindine-7,7-bisphosphonic acid;
octahydro-4-amino-1-thiobutyl-2-pyrindine-7,7-bisphosphonic acid;
octahydro-4-hydroxy-4-thiobutyl-2-pyrindine-7,7-bisphosphonic acid;
octahydro-7-(1-mercapto-1-methyl)ethyl-1-pyrindine-5,5-bisphosphonic acid;
octahydro-3-hydroxy-7-thiobutyl-1-pyrindine-5,5-bisphosphonic acid;
octahydro-3-dimethylamino-6-thiomethyl-1-pyrindine-5,5-bisphosphonic acid;
octahydro-7-thioethyl-1-pyrindine-5,5-bisphosphonic acid;
octahydro-6-hydroxy-7-thiopropyl-1-pyrindine-5,5-bisphosphonic acid;
octahydro-6-(1-mercapto-1-methyl)ethyl-1-pyrindine-5,5-bisphosphonic acid;
dihydro-2-mercapto-1-pyrindine-6,6-bisphosphonic acid;
dihydro-3-mercapto-1-pyrindine-6,6-bisphosphonic acid;
dihydro-4-mercapto-1-pyrindine-6,6-bisphosphonic acid;
dihydro-3-thiomethyl-1-pyrindine-6,6-bisphosphonic acid;
dihydro-3-thioethyl-1-pyrindine-6,6-bisphosphonic acid;
dihydro-3-thiopropyl-1-pyrindine-6,6-bisphosphonic acid;
dihydro-3-thiobutyl-1-pyrindine-6,6-bisphosphonic acid;
dihydro-2-thioethyl-1-pyrindine-6,6-bisphosphonic acid;
dihydro-4-thiopropyl-1-pyrindine-6,6-bisphosphonic acid;
dihydro-2-methoxy-4-thiobutyl-1-pyrindine-6,6-bisphosphonic acid;
dihydro-1-mercapto-2-pyrindine-6,6-bisphosphonic acid;
dihydro-3-mercapto-2-pyrindine-6,6-bisphosphonic acid;
dihydro-4-mercapto-2-pyrindine-6,6-bisphosphonic acid;
dihydro-4-thiomethyl-2-pyrindine-6,6-bisphosphonic acid;
dihydro-4-thioethyl-2-pyrindine-6,6-bisphosphonic acid;
dihydro-4-thiopropyl-2-pyrindine-6,6-bisphosphonic acid;
dihydro-4-thiobutyl-2-pyrindine-6,6-bisphosphonic acid;
dihydro-3-thioethyl-2-pyrindine-6,6-bisphosphonic acid;
dihydro-1-thiopropyl-2-pyrindine-6,6-bisphosphonic acid;
dihydro-1-methoxy-4-thiobutyl-2-pyrindine-6,6-bisphosphonic acid;
dihydro-4-amino-1-thiobutyl-2-pyrindine-6,6-bisphosphonic acid;
dihydro-4-hydroxy-4-thiobutyl-2-pyrindine-6,6-bisphosphonic acid;
dihydro-7-mercapto-1-pyrindine-6,6-bisphosphonic acid;
dihydro-5-mercapto-1-pyrindine-6,6-bisphosphonic acid;
dihydro-7-thiomethyl-1-pyrindine-6,6-bisphosphonic acid;
dihydro-7-thiobutyl-1-pyrindine-6,6-bisphosphonic acid;
dihydro-3-amino-7-mercapto-1-pyrindine-6,6-bisphosphonic acid;
dihydro-3-amino-5-thiopropyl-1-pyrindine-6,6-bisphosphonic acid;
dihydro-3-methoxy-7-(1-mercapto-1-methyl)ethyl-1-pyrindine-6,6-bisphosphonic acid;
dihydro-1-mercapto-2-pyrindine-7,7-bisphosphonic acid;
dihydro-3-mercapto-2-pyrindine-7,7-bisphosphonic acid;
dihydro-4-mercapto-2-pyrindine-7,7-bisphosphonic acid;
dihydro-4-thiomethyl-2-pyrindine-7,7-bisphosphonic acid;
dihydro-4-thioethyl-2-pyrindine-7,7-bisphosphonic acid;
dihydro-4-thiopropyl-2-pyrindine-7,7-bisphosphonic acid;
dihydro-4-thiobutyl-2-pyrindine-7,7-bisphosphonic acid;
dihydro-3-thioethyl-2-pyrindine-7,7-bisphosphonic acid;
dihydro-1-thiopropyl-2-pyrindine-7,7-bisphosphonic acid;
dihydro-1-methoxy-4-thiobutyl-2-pyrindine-7,7-bisphosphonic acid;
dihydro-4-amino-1-thiobutyl-2-pyrindine-7,7-bisphosphonic acid;
dihydro-4-hydroxy-4-thiobutyl-2-pyrindine-7,7-bisphosphonic acid;
dihydro-2-mercapto-1-pyrindine-7,7-bisphosphonic acid;
dihydro-3-mercapto-1-pyrindine-7,7-bisphosphonic acid;
dihydro-4-mercapto-1-pyrindine-7,7-bisphosphonic acid;
dihydro-3-thiomethyl-1-pyrindine-7,7-bisphosphonic acid;
dihydro-3-thioethyl-1-pyrindine-7,7-bisphosphonic acid;
dihydro-3-thiopropyl-1-pyrindine-7,7-bisphosphonic acid;
dihydro-3-thiobutyl-1-pyrindine-7,7-bisphosphonic acid;
dihydro-2-thioethyl-1-pyrindine-7,7-bisphosphonic acid;
dihydro-4-thiopropyl-1-pyrindine-7,7-bisphosphonic acid;
dihydro-2-methoxy-4-thiobutyl-1-pyrindine-7,7-bisphosphonic acid;
dihydro-7-(1-mercapto-1-methyl)ethyl-1-pyrindine-5,5-bisphosphonic acid;
dihydro-3-hydroxy-7-thiobutyl-1-pyrindine-5,5-bisphosphonic acid;
dihydro-3-dimethylamino-6-thiomethyl-1-pyrindine-5,5-bisphosphonic acid;
dihydro-7-thioethyl-1-pyrindine-5,5-bisphosphonic acid;
dihydro-6-hydroxy-7-thiopropyl-1-pyrindine-5,5-bisphosphonic acid;
dihydro-6-(1-mercapto-1-methyl)ethyl-1-pyrindine-5,5-bisphosphonic acid;
dihydro-1-mercapto-2-pyrindine-5,5-bisphosphonic acid;
dihydro-3-mercapto-2-pyrindine-5,5-bisphosphonic acid;
dihydro-4-mercapto-2-pyrindine-5,5-bisphosphonic acid;
dihydro-4-thiomethyl-2-pyrindine-5,5-bisphosphonic acid;
dihydro-4-thioethyl-2-pyrindine-5,5-bisphosphonic acid;
dihydro-4-thiopropyl-2-pyrindine-5,5-bisphosphonic acid;
dihydro-4-thiobutyl-2-pyrindine-5,5-bisphosphonic acid;
dihydro-3-thioethyl-2-pyrindine-5,5-bisphosphonic acid;

dihydro-1-thiopropyl-2-pyrindine-5,5-bisphosphonic acid;

dihydro-1-methoxy-4-thiobutyl-2-pyrindine-5,5-bisphosphonic acid;

dihydro-4-amino-1-thiobutyl-2-pyrindine-5,5-bisphosphonic acid;

dihydro-4-hydroxy-4-thiobutyl-2-pyrindine-5,5-bisphosphonic acid;

dihydro-2-mercapto-1-pyrindine-5,5-bisphosphonic acid;
dihydro-3-mercapto-1-pyrindine-5,5-bisphosphonic acid;
dihydro-4-mercapto-1-pyrindine-5,5-bisphosphonic acid;
dihydro-3-thiomethyl-1-pyrindine-5,5-bisphosphonic acid;

dihydro-3-thioethyl-1-pyrindine-5,5-bisphosphonic acid;
dihydro-3-thiopropyl-1-pyrindine-5,5-bisphosphonic acid;

dihydro-3-thiobutyl-1-pyrindine-5,5-bisphosphonic acid;
dihydro-2-thioethyl-1-pyrindine-5,5-bisphosphonic acid;
dihydro-4-thiopropyl-1-pyrindine-5,5-bisphosphonic acid;

dihydro-2-methoxy-4-thiobutyl-1-pyrindine-5,5-bisphosphonic acid;

and the pharmaceutically-acceptable salts and esters thereof.

The most preferred compound of the present invention is octahydro-7-(2-mercaptoethyl)-1-pyrindine-6,6-bisphosphonic acid, and the pharmaceutically-acceptable salts and esters thereof.

It is further desirable that the bicyclic compounds of the present invention have a "cis" ring juncture. Therefore, it is preferred, for example, that octahydro-7-(2-mercaptoethyl)-1-pyrindine-6,6-bisphosphonate have the structure:

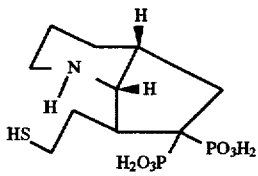

In order to determine and assess pharmacological activity, testing of the phosphonate compounds in animals is carried out using various assays known to those skilled in the art. Thus, the in vivo bone antiresorptive activity may be conveniently demonstrated using an assay designed to test the ability of these compounds to inhibit the resorption of bone, which bone resorption is characteristic of abnormal calcium and phosphate metabolism. Examples of such known tests include the Schenk model. Another useful art-known test is the adjuvant arthritis test. Also useful is the in vitro hydroxyapatite crystal growth inhibition test. These and other appropriate tests for pharmacological activity are disclosed and/or referred to in Shinoda et al., *Calcified Tissue International*, 35, pp 87–99 (1983); Schenk et al., *Calcified Tissue Research*, 11, pp 196–214 (1973); Russell et al., *Calcified Tissue Research*, 6, pp 183–196 (1970); Muhlbauer and Fleisch, *Mineral Electrolyte Metab.*, 5, pp 296–303 (1981); Nancollas et al., *Oral Biol.*, 15, 731 (1970); U.S. Pat. No. 3,683,080, to Francis, Issued Aug. 8, 1972; U.S. Pat. No. 4,134,969, to Schmidt-Dunker, Issued Jan. 16, 1979; and EPO Patent Application Publication No. 189,662, published Aug. 6, 1986; the disclosures of all these articles and patent specifications being incorporated herein by reference in their entirety. Certain of these tests for pharmacological activity are also described in more detail in the Examples provided hereinafter.

In addition to being useful for treating or preventing pathological conditions characterized by abnormal calcium or phosphate metabolism, the compounds of the present invention may have other uses. For example, the compounds of the present invention are believed to be useful as bone scanning agents after labeling with 99m-technetium. In addition, the compounds of the present invention are useful as sequestering agents for polyvalent metal ions, particularly di-(e.g. calcium and magnesium) and trivalent metal ions, (e.g. indium). Thus, the compounds of the present invention are useful as builders in detergents and cleansers, or for treating water. They are also useful as stabilizers for per-compounds. In addition, they may be useful in preventing the formation of tartar (i.e., calculus) and/or plaque on teeth. Finally, the compounds of the present invention may be useful as herbicides which are non-toxic to animals.

The thio-substituted, nitrogen-containing cyclic phosphonate compounds of the present invention can be made utilizing the methods set forth in Examples A–O herein.

Compositions Containing Novel Thio-Substituted Cyclic Phosphonate Compounds

The novel thio-substituted phosphonate compounds of the present invention may be administered to humans or other mammals by a variety of routes, including, but not limited to, oral dosage forms and injections (intravenous, intramuscular, intraperitoneal and subcutaneous). Numerous other dosage forms containing the novel thio-substituted phosphonate compounds of the present invention can be readily formulated by one skilled in the art, utilizing the suitable pharmaceutical excipients as defined below. For considerations of patient compliance, oral dosage forms are generally most preferred.

The term "pharmaceutical composition" as used herein means a combination comprised of a safe and effective amount of the thio-substituted phosphonate compound active ingredient, or mixtures thereof, and pharmaceutically-acceptable excipients.

The phrase "safe and effective amount", as used herein, means an amount of a compound or composition large enough to significantly positively modify the symptoms and/or condition to be treated, but small enough to avoid serious side effects (at a reasonable benefit/risk ratio), within the scope of sound medical judgment. The safe and effective amount of active ingredient for use in the pharmaceutical compositions to be used in the method of the invention herein will vary with the particular condition being treated, the age and physical condition of the patient being treated, the severity of the condition, the duration of the treatment, the nature of concurrent therapy, the particular active ingredient being employed, the particular pharmaceutically-acceptable excipients utilized, and like factors within the knowledge and expertise of the attending physician.

The term "pharmaceutically-acceptable excipients" as used herein includes any physiologically inert, pharmacologically inactive material known to one skilled in the art, which is compatible with the physical and chemical characteristics of the particular phosphonate compound active ingredient selected for use. Pharmaceutically-acceptable excipients include, but are not limited to, polymers, resins, plasticizers, fillers, binders, lubricants, glidants, disintegrants, solvents, co-solvents, buffer systems, surfactants, preservatives, sweetening agents, flavoring agents, pharmaceutical grade dyes or pigments, and viscosity agents.

The term "oral dosage form" as used herein means any pharmaceutical composition intended to be systemically administered to an individual by delivering said composition to the gastrointestinal tract of an individual, via the mouth of said individual. For purposes of the present invention, the delivered form can be in the form of a tablet, coated or non-coated; solution; suspension; or a capsule, coated or non-coated.

The term "injection" as used herein means any pharmaceutical composition intended to be systemically administered to a human or other mammal, via delivery of a solution or emulsion containing the active ingredient, by puncturing the skin of said individual, in order to deliver said solution or emulsion to the circulatory system of the individual either by intravenous, intramuscular, intraperitoneal or subcutaneous injection.

The rate of systemic delivery can be satisfactorily controlled by one skilled in the art, by manipulating any one or more of the following:

(a) the active ingredient proper;
(b) the pharmaceutically-acceptable excipients; so long as the variants do not interfere in the activity of the particular active ingredient selected;
(c) the type of the excipient, and the concomitant desirable thickness and permeability (swelling properties) of said excipients;
(d) the time-dependent conditions of the excipient itself and/or within the excipients;
(e) the particle size of the granulated active ingredient; and
(f) the pH-dependent conditions of the excipients.

In particular, the solubility, acidity, and susceptibility to hydrolysis of the different thio-substituted phosphonate active ingredients, such as acid addition salts, salts formed with the carboxylic group, e.g., alkali metal salts, alkaline earth metal salts, etc., and esters, e.g., alkyl, alkenyl, aryl, aralkyl, may be used as guidelines for the proper choice. In addition, suitable pH-conditions might be established within the oral dosage forms by adding a suitable buffer to the active ingredient in accordance with the desired release pattern.

As stated hereinabove, pharmaceutically-acceptable excipients include, but are not limited to, resins, fillers, binders, lubricants, solvents, glidants, disintegrants co-solvents, surfactants, preservatives, sweetener agents, flavoring agents, buffer systems, pharmaceutical-grade dyes or pigments, and viscosity agents.

The preferred solvent is water.

Flavoring agents among those useful herein include those described in *Remington's Pharmaceutical Sciences*, 18th Edition, Mack Publishing Company, 1990, pp. 1288–1300, incorporated by reference herein. The pharmaceutical compositions suitable for use herein generally contain from 0–2% flavoring agents.

Dyes or pigments among those useful herein include those described in *Handbook of Pharmaceutical Excipients*, pp. 81–90, 1986 by the American Pharmaceutical Association & the Pharmaceutical Society of Great Britain, incorporated by reference herein. The pharmaceutical compositions herein generally contain from 0–2% dyes or pigments.

Preferred co-solvents include, but are not limited to, ethanol, glycerin, propylene glycol, polyethylene glycols. The pharmaceutical compositions of the present invention include from 0–50% co-solvents.

Preferred buffer systems include, but are not limited to, acetic, boric, carbonic, phosphoric, succinic, malaic, tartaric, citric, acetic, benzoic, lactic, glyceric, gluconic, glutaric and glutamic acids and their sodium, potassium and ammonium salts. Particularly preferred are phosphoric, tartaric, citric, and acetic acids and salts. The pharmaceutical composition of the present invention generally contain from 0–5% buffer systems.

Preferred surfactants include, but are not limited to, polyoxyethylene sorbitan fatty acid esters, polyoxyethylene monoalkyl ethers, sucrose monoesters and lanolin esters and ethers, alkyl sulfate salts, sodium, potassium, and ammonium salts of fatty acids. The pharmaceutical compositions of the present invention include 0–2% surfactants.

Preferred preservatives include, but are not limited to, phenol, alkyl esters of parahydroxybenzoic acid, o-phenylphenol benzoic acid and the salts thereof, boric acid and the salts thereof, sorbic acid and the salts thereof, chlorobutanol, benzyl alcohol, thimerosal, phenylmercuric acetate and nitrate, nitromersol, benzalkonium chloride, cetylpyridinium chloride, methyl paraben, and propyl paraben. Particularly preferred are the salts of benzoic acid, cetylpyridinium chloride, methyl paraben and propyl paraben. The compositions of the present invention generally include from 0–2% preservatives.

Preferred sweeteners include, but are not limited to, sucrose, glucose, saccharin, sorbitol, mannitol, and aspartame. Particularly preferred are sucrose and saccharin. Pharmaceutical compositions of the present invention include 0–5% sweeteners.

Preferred viscosity agents include, but are not limited to, methylcellulose, sodium carboxymethylcellulose, hydroxypropylmethylcellulose, hydroxypropylcellulose, sodium alginate, carbomer, povidone, acacia, guar gum, xanthan gum and tragacanth. Particularly preferred are methylcellulose, carbomer, xanthan gum, guar gum, povidone, sodium carboxymethylcellulose, and magnesium aluminum silicate. Compositions of the present invention include 0–5% viscosity regents.

Preferred fillers include, but are not limited to, lactose, mannitol, sorbitol, tribasic calcium phosphate, dibasic calcium phosphate, compressible sugar, starch, calcium sulfate, dextro and microcrystalline cellulose. The compositions of the present invention contain from 0–75% fillers.

Preferred lubricants include, but are not limited to, magnesium stearate, stearic acid, and talc. The pharmaceutical compositions of the present invention include 0.5–2% lubricants.

Preferred glidants include, but are not limited to, talc and colloidal silicon dioxide. The compositions of the present invention include from 1–5% glidants.

Preferred disintegrants include, but are not limited to, starch, sodium starch glycolate, crospovidone, croscarmelose sodium, and microcrystalline cellulose. The pharmaceutical compositions of the present invention include from 4–15% disintegrants.

Preferred binders include, but are not limited to, acacia, tragacanth, hydroxypropylcellulose, pregelatinized starch, gelatin, povidone, hydroxypropylcellulose, hydroxypropylmethylcellulose, methylcellulose, sugar solutions, such as sucrose and sorbitol, and ethylcellulose. The compositions of the present invention include 1–10% binders.

Compounds of the present invention may comprise from about 0.1% to about 99.9% by weight of the pharmaceutical compositions of the present invention. Preferably, the compounds of the present invention comprise from about 20% to about 80% by weight of the pharmaceutical compositions of the present invention.

Accordingly, the pharmaceutical compositions of the present invention include from 15–95% of a thio-substituted phosphonate compound active ingredient, or mixture, thereof; 0–2% flavoring agents; 0–50% co-solvents; 0–5% buffer system; 0–2% surfactants; 0–2% preservatives; 0–5% sweeteners; 0–5% viscosity agents; 0–75% fillers; 0.5–2% lubricants; 1–5% glidants; 4–15% disintegrants; and 1–10% binders.

The choice of a pharmaceutically-acceptable carrier to be used in conjunction with the phosphonate compound of the present invention is basically determined by the way the phosphonate compound is to be administered. If the compound is to be injected, the preferred pharmaceutical carrier is sterile physiological saline, the pH of which has been adjusted to about 7.4. Suitable pharmaceutically-acceptable carriers for topical application include those suited for use in creams, gels, tapes and the like.

The term "mg P", as used herein, means the weight of the phosphorus atoms present in an amount of a phosphonic acid compound of the present invention. This unit is used to standardize the amount of the phosphonic acid compounds of the present invention to be used in the pharmaceutical compositions and methods of the present inventions. For example, octahydro-3-mercapto-1-pyrindine-6,6-bisphosphonic acid has a molecular weight of 317 g/mole, of which 19.6% (62 g/mole) is due to the two phosphorus atoms present in this molecule. One milligram of this compound is therefore calculated to have 0.196 mg P (1 mg×19.6%). Thus, to prepare a pharmaceutical composition containing 0.1 mg P of this compound, the composition should contain 0.51 mg of the compound; and to dose 0.10 mg P/kg of this compound to a 50 kg patient, the patient would be dosed with 25.5 mg of this compound.

The pharmaceutically-acceptable carrier employed in conjunction with the phosphonate compounds of the present invention is used at a concentration sufficient to provide a practical size to dosage relationship. The pharmaceutically-acceptable carriers, in total, may comprise from about 0.1% to about 99.9% by weight of the pharmaceutical compositions of the present invention, and preferably from about 20% to about 80%.

Suitable pharmaceutical compositions are described herein in Examples R-T. It is well within the capabilities of one skilled in the art to vary the non-limiting examples described herein to achieve a broad range of pharmaceutical compositions.

Method for Treating or Preventing Diseases Characterized by Abnormal Calcium and Phosphate Metabolism Another aspect of the present invention is methods for treating or preventing diseases characterized by abnormal calcium and phosphate metabolism. Such methods comprise administering to a human or other mammal in need of such treatment a safe and effective amount of a thio-substituted cyclic containing phosphonate compound of the present invention.

The preferred mode of administering the phosphonate compound of the present invention is orally. The preferred unit dosage form is therefore tablets, capsules and the like, comprising a safe and effective amount of the phosphonate compound of the present invention. Preferably, the compositions comprise from about 1 mg P to about 600 mg P of a phosphonate compound of the present invention. Pharmaceutically-acceptable carriers suitable for the preparation of unit dosage forms for oral administration are well known in the art. Their selection will depend on secondary considerations like taste, cost, and shelf stability, which are not critical for the purposes of the present invention, and can be made without difficulty by a person skilled in the art.

The term "abnormal calcium and phosphate metabolism", as used herein, means (1) conditions which are characterized by anomalous mobilization of calcium and phosphate leading to general or specific bone loss, or excessively high calcium and phosphate levels in the fluids of the body; and (2) conditions which cause or result from deposition of calcium and phosphate anomalously in the body. The first category includes, but is not limited to, osteoporosis, Paget's disease, hyperparathyroidism, hypercalcemia of malignancy, heterotopic ossification, and osteolytic bone metastases. The second category includes, but is not limited to, myositis ossificans progressiva, calcinosis universalis, and such afflictions as arthritis (especially rheumatoid arthritis and osteoarthritis), neuritis, bursitis, tendonitis and other conditions which predispose involved tissue to deposition of calcium phosphates.

The term "rheumatoid arthritis" as used herein, means a chronic systemic and articular inflammatory disorder of unknown etiology. It is characterized by destruction of articular cartilage, ligaments, tendons, and bone.

The term "osteoarthritis" as used herein, means a non-inflammatory disorder of the movable joints. It is characterized by deterioration and abrasion of the articular cartilage; and new bone formation at the joint surface.

The term "person at risk" and "person in need of such treatment", as used herein, mean any human or other mammal which suffers a significant risk of abnormal calcium and phosphate metabolism if left untreated, and any human or other mammal diagnosed as being afflicted with abnormal calcium and phosphate metabolism and any human or lower animal at risk of rheumatoid arthritis or osteoarthritis or afflicted with rheumatoid arthritis or osteoarthritis. For example, persons at risk of osteoporosis include postmenopausal women; persons undergoing certain steroid therapy; persons on certain anti-convulsant drugs; persons diagnosed as having Paget's disease, hyperparathyroidism, hypercalcemia of malignancy, or osteolytic bone metastases; persons diagnosed as suffering from one or more of the various forms of osteoporosis; persons belonging to a population group known to have a significantly higher than average chance of developing osteoporosis, e.g., postmenopausal women, men over age 65, and persons being treated with drugs known to cause osteoporosis as a side effect; persons diagnosed as suffering from myositis ossificans progressiva or calcinosis universalis, and persons having adverse health habits, such as little physical activity, low dietary calcium, cigarette smoking and alcohol abuse, and persons afflicted with rheumatoid arthritis. Persons at risk of rheumatoid arthritis and osteoarthritis include all racial and ethnic groups. Yet women in the 4–6th decades of life are generally more often affected.

The phrase "safe and effective amount", as used herein, means an amount of a compound or composition high enough to significantly positively modify the condition to be treated, but low enough to avoid serious side effects (at a reasonable benefit/risk ratio), within the scope of sound medical judgment. The safe and effective amount of phosphonate compounds of the present invention will vary with the particular condition being treated, the age and physical condition of the patient being treated, the severity of the condition, the duration of the treatment, the nature of concurrent therapy, the specific diphosphonate employed, the particular pharmaceutically-acceptable carrier utilized, and like factors within the knowledge and expertise of the attending physician. However, single dosages can range from about 0.01 mg P to about 3500 mg P, or from about 0.0002 to about 70 mg P/kg of body weight (based on a body weight of 50 kg). Preferred single dosages are from about 1 mg P to about 600 mg P, or from about 0.02 to about 12 mg P/kg of body weight (based on a body weight of 50 kg). Up to about four single dosages per day may be administered. Daily dosages greater than about 500 mg P/kg are not required to produce the desired effect and may produce undesirable side effects. The higher dosages within this range are, of course, required in the case of oral administration because of limited absorption.

The following Examples further describe and demonstrate the preferred embodiments within the scope of the present invention. The Examples are given solely for the purpose of illustration, and are not to be construed as limitations of the present invention since many variations thereof are possible without departing from its spirit and scope.

EXAMPLE A

Synthesis of Dihydro-7-Mercapto-1-pyrindine-6,6-bisphosphonic acid

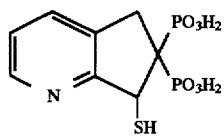

Dihydro-7-mercapto-1-pyrindine-6,6-bisphosphonic acid is prepared and synthesized as described hereinbelow.

I. Synthesis of Dihydro-1-pyrindine-6,6-diphosphonic acid tetraethyl ester

To an ice bath chilled solution of 35% potassium hydride in mineral oil (5.2 g; 0.045 moles) stirring under argon in 70 ml of DMSO (dry) is added a solution of tetraisopropyl-methanediphosphonate (7.82 g; 0.023 moles) in 30 ml of DMSO. On completion of a dropwise addition, the resulting solution is stirred at room temperature for one hour. A solution of 2,3-bis(chloromethyl)pyridine (4.0 g; 0.023 mole) (crude product as isolated by K. Tsuda et.al., Chem Pharm Bull., 1, (1953), 142) in 15 ml of DMSO is slowly added and the reaction mixture is then heated at 90° C. for 1 hour. After cooling, the DMSO is removed under vacuum. 2.1 g (21%) of the desired product is purified via flash chromatography using a 5–15% ethanol in methylene chloride gradient on silica gel.

II. Synthesis of Dihydro-7-thiobenzyl-1-pyrindine-6,6-bis phosphonic acid, tetraethyl ester To a solution of dihydro-1-pyrindine-6,6-bisphosphonic acid, tetraethyl ester (7.0 mmol) in anhydrous THF (100 ml) at −78° C. under argon is added dropwise a pregenerated solution of lithium diisopropyl amide (7.0 mmol) in THF (10 ml). After stirring 30 minutes, to this is added benzyldisulfide (7.2 mmol) in THF (25 ml). The reaction mixture is allowed to warm to room temperature and stirred for 18 hours. The reaction is quenched by the addition of saturated aqueous ammonium chloride and then extracted with diethyl ether. The organic layers are combined, dried over sodium sulfate, filtered and concentrated under reduced pressure. The desired product is purified by flash chromatography using a 5–10% isopropanol in methylene ethylene chloride gradient on silica gel.

III. Synthesis of Dihydro-7-thiobenzyl-1-pyrindine-6,6-bisphosphonic acid

The ester (5.0 mmol) is added to 6N HCl (50 ml) and heated at reflux for 18 hours under an atmosphere of argon. The reaction mixture is cooled and then concentrated under reduced pressure. The crude residue is recrystallized from water and ethanol.

IV. Synthesis of Dihydro-7-Mercapto-1-pyrindine-6,6-bisphosphonic acid

Dihydro-7-thiobenzyl-1-pyrindine-6,6-bisphosphonic acid (1.8 mmol) is added to freshly distilled ammonia (200 ml) at −78° C. followed by the addition of small pieces of sodium. Enough sodium is added to maintain a blue color for 20 minutes. The reaction mixture is then quenched by the addition of isobutylene. The ammonia is allowed to evaporate and the crude residue is dissolved in water and the desired product is precipitated by the addition of isopropanol.

EXAMPLE B

Synthesis of Octahydro-7-Mercapto-1-pyrindine-6,6-bisphosphonic acid

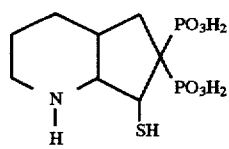

Octahydro-7-mercapto-1-pyrindine-6,6-bisphosphonic acid is prepared as described below.

Dihydro-7-mercapto-1-pyrindine-6,6-bisphosphonic acid (0.5 mmol) [prepared as described in Example A hereinbefore], distilled water (100 ml) and PtO$_2$ (0.5 g) are placed in a 500 ml Parr hydrogenation bottle. The mixture is hydrogenated at room temperature (40 psi) for 48 hours. The solution is filtered through celite and washed with hot water. The filtrate is then concentrated under reduced pressure and the desired product is obtained in good purity by further drying the resultant solid overnight under vacuum.

EXAMPLE C

Synthesis of Dihydro-7-(2-mercaptoethyl)-1-pyrindine-6,6-bisphosphonic acid

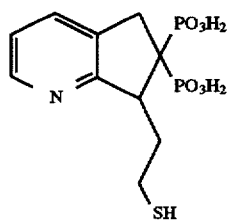

Dihydro-7-(2-mercaptoethyl)-1-pyrindine-6,6-bisphosphonic acid is prepared and synthesized as described hereinbelow.

1. Synthesis of Dihydro-7-(2-acetylthioethyl)-1-pyrindine-6,6-bisphosphonic acid, tetraethyl ester To a solution of dihydro-1-pyrindine-6,6-bisphosphonic acid, tetraethyl ester (7.0 mmol) [prepared as described in Example A, Part I] in anhydrous THF (100 ml) at −78° C. under argon is added dropwise a pregenerated solution of lithium diisopropyl amide (7.0 mmol) in THF (10 ml). After stirring 30 minutes, to this is added 2-acetylthio-1-iodoethane (7.5 mmol) in THF (25 ml). The reaction mixture is stirred at −78° C. for 5 hours then allowed to warm to room temperature and stirred overnight. The reaction is quenched by the addition of saturated aqueous ammonium chloride and then extracted with diethyl ether. The organic layers are combined, dried over sodium sulfate, filtered and concentrated under reduced pressure. The desired product is purified by flash chromatography using a 5–10% isopropanol in methylene chloride gradient on silica gel.

II. Synthesis of Dihydro-7-(2-mercaptoethyl)-1-pyrindine-6,6-bisphosphonic acid

Dihydro-7-(2-acetylthioethyl)-1-pyrindine-6,6-bisphosphonic acid, tetraethyl ester (4.0 mmol) is added to 6N HCl (35 ml) and heated at reflux under nitrogen for 18 hours. The reaction mixture is then cooled and concentrated under reduced pressure. The product is obtained by recrystallizing from water and isopropanol.

EXAMPLE D

Synthesis of Octahydro-7-(2-mercaptoethyl)-1-pyrindine-6,6-bisphosphonic acid

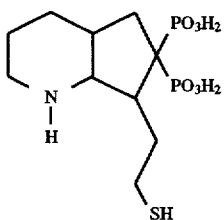

Octahydro-7-(2-mercaptoethyl)-1-pyrindine-6,6-bisphosphonic acid is prepared as described below.

Using essentially the same procedure as in Example B, dihydro-7-(2-mercaptoethyl)-1-pyrindine-6,6-bisphosphonic acid [prepared as described in Example C hereinbefore] is hydrogenated to provide octahydro-7-(2-mercaptoethyl)-1-pyrindine-6,6-bisphosphonic acid.

EXAMPLE E

Synthesis of Dihydro-3-mercapto-1-pyrindine-6,6-bisphosphonic acid

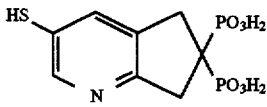

Dihydro-3-mercapto-1-pyrindine-6,6-bisphosphonic acid is prepared and synthesized as described hereinbelow.

I. Synthesis of Dihydro-3-bromo-1-pyrindine 6,6-bisphosphonic acid, tetraethyl ester (a) Various substituted dihydro-1-pyrindine-6,6-diphosphonic acid compounds can be prepared as described in Example A (part I) by using as the starting material the appropriately substituted 2,3-bis(chloromethyl)pyridine. Such substituted starting materials may be prepared by (1) photochemically reacting substituted 2,3-dimethyl pyridine with N-chlorosuccinimide in CCl$_4$; or (2) esterifying substituted 2,3-dicarboxy pyridine with MeOH/H+, followed by reduction with LiAlH$_4$, and then chlorination with SOCl$_2$.

(b) Using the above methodology, 5-bromo-2,3-lutidine can be converted to 5-bromo-2,3-bis(chloromethyl)pyridine. Then using essentially the same procedure as described in Example A (part I), 5-bromo-2,3-bis(chloromethyl)pyridine is converted to dihydro-3-bromo-1-pyrindine-6,6-bisphosphonic acid, tetraethyl ester.

II. Synthesis of Dihydro-3-thio-t-butyl-1-pyrindine-6,6-bisphosphonic acid, tetraethyl ester To a solution of dihydro-3-bromo-1-pyrindine-6,6-bisphosphonic acid, tetraethyl ester (4.39 g, 10 mmol) in THF (10 ml) cooled to −78° is added a solution of n-butyllithium (2.1 equivalent) in hexane over 30 minutes. The reaction is kept at −78° C. for an additional 30 minutes.

To this solution is added tert-butyl disulfide (2.2 equivalent) and the reaction is allowed to warm to room temperature over 30 minutes. After standard aqueous work-up dihydro-3-thio-t-butyl-1-pyrindine-6,6-bisphosphonic acid, tetraethyl ester is isolated and used in the next reaction without purification.

III. Synthesis of Dihydro-3-mercapto-1-pyrindine-6,6-bisphosphonic acid

A solution of dihydro-3-thio-t-butyl-1-pyrindine-6,6-bisphosphonic acid, tetraethyl ester in 2.5M HCl is heated to reflux for 12 hr. The reaction mixture is then cooled and concentrated under reduced pressure. The solid residue is triturated with acetone and then recrystallized from water and ethanol yielding dihydro-3-mercapto-1-pyrindine-6,6-bisphosphonic acid.

EXAMPLE F

Synthesis of Octahydro-3-mercapto-1-pyrindine-6,6-bisphosphonic acid

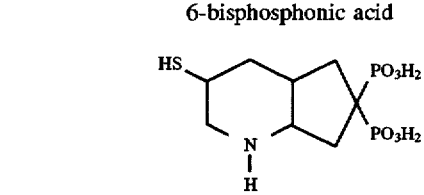

Octahydro-3-mercapto-1-pyrindine-6,6-bisphosphonic acid is prepared as described below.

Dihydro-3-mercapto-1-pyrindine-6,6-bisphosphonic acid (0.5 mmol) [prepared as described in Example E hereinbefore], distilled water (100 ml) and PtO$_2$ (0.5 g) are placed in a 500 ml Parr hydrogenation bottle. The mixture is hydrogenated at room temperature (40 psi) for 48 hours. The solution is filtered through celite and washed with hot water. The filtrate is then concentrated under reduced pressure and the desired product is obtained in good purity by further drying the resultant solid overnight under vacuum.

EXAMPLE G

Synthesis of Dihydro-4-mercapto-2-pyrindine-6,6-bisphosphonic acid

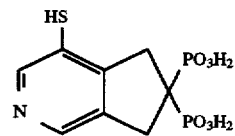

Dihydro-4-mercapto-2-pyrindine-6,6-bisphosphonic acid is prepared as described below.

I. Synthesis of Dihydro-4-bromo-2-pyrindine-6,6-bisphosphonic acid, tetraethyl ester As described in Example E (part Ia), 5-bromo-3,4-lutidine is converted to 5-bromo-3,4-bis(chloromethyl)pyridine.

Using essentially the same procedure as described in Example A (part I) hereinbefore, 5-bromo-3,4-bis(chloromethyl) pyridine is converted into dihydro-4-bromo-2-pyrindine-6,6-bisphosphonic acid, tetraethyl ester.

II. Synthesis of Dihydro-4-thio-t-butyl-2-pyrindine-6,6-bisphosphonic acid, tetraethyl ester Using essentially the same procedure as described in Example E (part II) hereinbefore, dihydro-4-bromo-2-pyrindine-6,6-bisphosphonic acid, tetraethyl ester is converted into dihydro-4-thio-t-butyl-2-pyrindine-6,6-bisphosphonic acid, tetraethyl ester.

III. Synthesis of Dihydro-4-mercapto-2-pyrindine-6,6-bisphosphonic acid

Using essentially the same procedure as described in Example E (part III) hereinbefore, dihydro-4-thio-t-butyl-2-pyrindine-6,6-bisphosphonic acid, tetraethyl ester is converted into dihydro-4-mercapto-2-pyrindine-6,6-bisphosphonic acid.

EXAMPLE H

Synthesis of Octahydro-4-mercapto-2-pyrindine-6,6-bisphosphonic acid

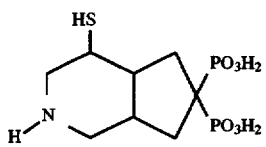

Octahydro-4-mercapto-2-pyrindine-6,6-bisphosphonic acid is prepared as described below.

Dihydro-4-mercapto-2-pyrindine-6,6-bisphosphonic acid (0.5 mmol) [prepared as described in Example G hereinbefore], distilled water (100 ml) and $PtO_2$ (0.5 g) are placed in a 500 ml Parr hydrogenation bottle. The mixture is hydrogenated at room temperature (40 psi) for 48 hours. The solution is filtered through celite and washed with hot water. The filtrate is then concentrated under reduced pressure and the desired product is obtained in good purity by further drying the resultant solid overnight under vacuum.

EXAMPLE I

Synthesis of Dihydro-3-(4-mercaptobutyl)-1-pyrindine-6,6-bisphosphonic acid

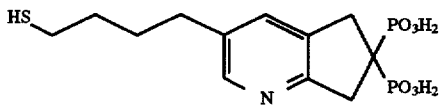

Dihydro-3-(4-mercaptobutyl)-1-pyrindine-6,6-bisphosphonic acid is prepared and synthesized as described hereinbelow.

I. Synthesis of Dihydro-3-(4-hydroxybutyl)-1-pyrindine-6,6-bisphosphonic acid, tetraethyl ester To a solution of dihydro-3-bromo-1-pyrindine-6,6-bisphosphonic acid, tetraethyl ester (10 mmol) [prepared as described in Example E (part I) hereinbefore] in THF (10 ml) cooled to −78° C. is added a solution of n-butyllithium (2.1 equivalent) in hexane over 30 minutes. The reaction is kept at −78° C. for an additional 30 minutes. To this solution is added 4-iodobutanol trimethylsilyl (TMS) ether (2.5 equivalent) and the reaction is allowed to warm to room temperature over 30 minutes. After standard aqueous work-up, dihydro-3-(4-butanol, TMS ether)-1-pyrindine-6,6-bisphosphonic acid, tetraethyl ester is isolated and used in the next reaction without purification.

Cleavage of the TMS ether from the product is accomplished by stirring it in THF and adding a solution of tetrabutylammonium fluoride (1M in THF) dropwise over 30 minutes. After a standard aqueous workup the resulting primary alcohol is isolated as an oil and used directly in the next reaction.

II. Synthesis of Dihydro-3-(4-bromobutyl)-1-pyrindine-6,6-bisphosphonic acid, tetraethyl ester A mixture of dihydro-3-(4-hydroxybutyl)-1-pyrindine-6,6-bisphosphonic acid, tetraethyl ester (10 mmol) carbon tetrabromide (11 mmol) and triphenyl phosphine (11 mmol), in dichloromethane (100 ml) is stirred at room temperature for 5 h. Water is added and the product is extracted with dichloromethane. The combined organic extracts are dried and concentrated. The residue is purified by flash column chromatography to give dihydro-3-(4-bromobutyl)-1-pyrindine-6,6-bisphosphonic acid, tetraethyl ester.

III. Synthesis of Dihydro-3-(4-acetylthiobutyl)-1-pyrindine-6,6-bisphosphonic acid, tetraethyl ester A solution of dihydro-3-(4-bromobutyl)-1-pyrindine-6,6-bisphosphonic acid, tetraethyl ester (5.0 mmol) is stirred in dry acetone (35 ml) and sodium thioacetate (5.2 mmol) is added. The mixture is stirred at 50° C. for 12 hours. After cooling to room temperature the solvent is removed under reduced pressure. The crude residue is dissolved in methylene chloride and washed with water. The organic layer is then dried and concentrated under reduced pressure. The desired product is purified by flash chromatography using a 5–10% isopropanol in methylene chloride gradient on silica gel.

IV. Synthesis of Dihydro-3-(4-mercaptobutyl)-1-pyrindine-6,6-bisphosphonic acid

Dihydro-3-(4-thioacetylbutyl)-1-pyrindine-6,6-bisphosphonic acid, tetraethyl ester (3.5 mmol) is dissolved in 2.5M HCl (50 ml) and is heated to reflux for 3 hours. The reaction mixture is cooled and concentrated under reduced pressure. The solid residue is triturated with acetone and then recrystallized from water and ethanol yielding dihydro-3-(4-mercaptobutyl)-1-pyrindine-6,6-bisphosphonic acid.

EXAMPLE J

Synthesis of Octahydro-3-(4-mercaptobutyl)-1-pyrindine-6,6-bisphosphonic acid

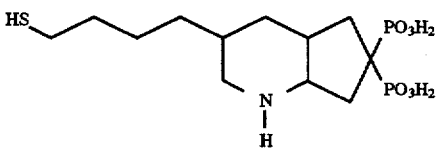

Octahydro-3-(4-mercaptobutyl)-1-pyrindine-6,6-bisphosphonic acid is prepared as described below.

Using essentially the same hydrogenation procedure as described in Example F hereinbefore, dihydro-3-(4-mercaptobutyl)-1-pyrindine-6,6-bisphosphonic acid [prepared as described in Example I hereinbefore] is converted into octahydro-3-(4-mercaptobutyl)-1-pyrindine-6,6-bisphosphonic acid.

EXAMPLE K

Synthesis of Dihydro-4-(4-mercaptobutyl)-2-pyrindine-6,6-bisphosphonic acid

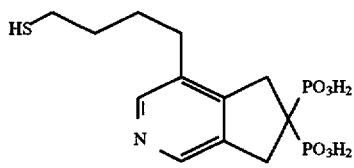

Dihydro-4-(4-mercaptobutyl)-2-pyrindine-6,6-bisphosphonic acid is prepared as described below.

Using essentially the same sequence of reactions as described in Example I hereinbefore, dihydro-4-bromo-2-pyrindine-6,6-bisphosphonic acid, tetraethyl ester [prepared as described in Example G hereinbefore] is converted into dihydro-4-(4-mercaptobutyl)-2-pyrindine-6,6-bisphosphonic acid.

EXAMPLE L

Synthesis of Octahydro-4-(4-mercaptobutyl)-2-pyrindine-6,6-bisphosphonic acid

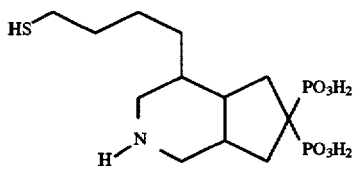

Octahyro-4-(4-mercaptobutyl)-2-pyrindine-6,6-bisphosphonic acid is prepared as described below.

Using essentially the same hydrogenation procedure as described in Example F hereinbefore, dihydro-4-(4-mercaptobutyl)-2-pyrindine-6,6-bisphosphonic acid [prepared as described in Example K hereinbefore] is converted into octahydro-4-(4-mercaptobutyl)-2-pyrindine-6,6-bisphosphonic acid.

EXAMPLE M

Synthesis of [1-hydroxy-(dihydro-7-mercapto-2-pyrind-7-yl) methylene]bis[phosphonic acid

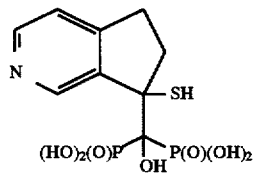

I. Synthesis of N-(2,2-diethoxyethyl)-N-[(3-methoxyphenyl) methyl]-4-methylbenzenesulfonamide m-Anisaldehyde (112 g, 0.82 mol) and aminoacetaldehyde diethyl acetal (115 g, 0.86 mmol) in benzene (2.6 1) are heated at reflux under an atmosphere of nitrogen for 3 hours. Approximately 1.8 of benzene is then removed by concentration under reduced pressure. The remaining solution is placed in a Parr hydrogenation vessel and hydrogenated at room temperature until the theoretical amount of hydrogen (56 lb.) is taken up. The solution is then filtered through celite and the filtrate is concentrated under reduced pressure. The resulting oil is dissolved in pyridine (1 l) and to this is added dropwise p-methoxybenzene sulfonyl chloride (172 g, 0.90 mol) in pyridine (600 ml). The reaction mixture is allowed to stir for 3 days at room temperature and then concentrated under reduced pressure. The residue is poured into ice water and stirred at 0° C. for 1 hour. The aqueous mixture is extracted with diethyl ether (6×500 ml). The combined organic extracts are washed with saturated aqueous NaCl, dried over magnesium sulfate, filtered and concentrated under reduced pressure to provide the product (312 g) in a 93% yield as a yellow oil.

II. Synthesis of 7-Methoxyisoquinoline

To a 2 liter round bottom flask equipped with a magnetic stir bar, condenser and nitrogen inlet is added (75 g, 0.184 mole) of N-(2,2-diethoxyethyl)-N-[(3-methoxyphenyl) methyl]-4-methyl-benzenesulfonamide, 1.0 liter of dioxane and 200 ml of 6N HCl. This slurry is stirred and heated at reflux under nitrogen for 18 hours. The reaction solution is then slowly poured into 1 liter of $H_2O$ and stirred for an additional 30 minutes then extracted with ether (2×500 ml). The pH of the aqueous layer is adjusted to 8 with ammonium hydroxide, the product is extracted with dichloromethane. The combined organics extracts are dried over $MgSO_4$, filtered and evaporated to yield 30 g of an oil. The crude product is purified by chromatography with 12.0% acetone in dichloromethane to provide the product (19.7 g) in a 67% yield.

III. Synthesis of 7-Hydroxyisoquinoline

To a 2-liter, 3-necked round bottom flask equipped with a magnetic stir bar and addition funnel is added 19.7 g (0.124 mole) of 7-methoxyisoquinoline and 800 ml of dry dichloromethane. This solution is stirred and cooled to −75° C. with a dry ice/acetone bath, 628 ml (0.628 mole) of 1.0M boron tribromide in dichloromethane is added dropwise maintaining the temperature at −75° C. Thereafter the slurry is stirred for 18 hours allowing the temperature to rise to room temperature. The reaction slurry is poured into 1 liter of ice water and stirred for an hour. The layers are separated and the aqueous layer is then adjusted from acidic to neutral (pH 7) with 1N NaOH. A yellow solid precipitates and is filtered off, then air dried to yield 14.5 g of a yellow solid, 81%.

IV. Synthesis of 7-Hydroxy-8-nitroisoquinoline

To a 300 ml round bottom flask is added 14.5 g (0.1 mole) of 7-hydroxyisoquinoline and 100 ml of warmed tetramethylene sulfone. The brown slurry is stirred and to it is added portionwise 18.6 g (0.14 mole) of nitronium tetrafluoroborate with cooling (ice bath). The reaction is stirred for 3 hours. The reaction is then quenched with 100 ml of methanol, evaporated to dryness and triturated twice with ether to precipitate a dark solid (19.0 g, 100%).

V. Synthesis of 8-Amino-7-hydroxyisoquinoline HCl salt

A hydrogenation jar is charged with 7-hydroxy-8-nitroisoquinoline (28.5 g, 0.15 mol), 5% Pd on carbon (6.0 g) and ethanol (725 ml). The slurry is hydrogenated (40 psi) until hydrogen uptake stops. The reaction mixture is then filtered through celite and the filtrate is concentrated under reduced pressure. The residue is dissolved in methanol. Addition of etheric-HCl precipitates the product as an HCl salt (19 g) in 65% yield.

VI. Synthesis of 7-hydroxy-8-isoquinolinediazonium chloride

To 8-amino-7-hydroxyisoquinoline HCl salt (4.94 g, 0.025 mol) in ethanolic-HCl at 0° C. is added dropwise a solution of tert-butylnitrite (17.46 ml), ethanol (790 ml) and water (58 ml). Following completion of the addition, the solution is stirred an additional 2 hours at 0° C. The product is precipitated from the reaction mixture by the addition of diethyl ether (2 l). The product is collected by filtration and rinsed with diethyl ether to provide the desired product (2.6 g) in 50% yield.

VII. Synthesis of 2-pyrindine-7-carboxylic acid, methyl ester

7-Hydroxy-8-isoquinolinediazonium chloride (0.50 g, 2.4 mmol) and sodium bicarbonate (302 mg, 3.6 mmol) in anhydrous methanol (650 ml) is irradiated with a 275 watt sunlamp at 0° C. for 3 hours. The reaction mixture is evaporated to dryness under vacuum. The crude residue is dissolved in water and the product is extracted in methylene chloride. The combined organic extracts are dried over magnesium sulfate, filtered and concentrated under reduced pressure to provide the product as an orange solid (210 mg) in 50% yield.

VIII. Synthesis of Dihydro-2-pyrindine-7-carboxylic acid, methyl ester

A hydrogenation bottle is charged with 2-pyrindine-7-carboxylic acid, methyl ester (0.8 g, 4.57 mmol), 5% Pd on carbon (2.0 g, wet) and methanol (125 ml). The slurry is hydrogenated (40 psi) until hydrogen uptake stops. The reaction mixture is filtered through celite and then evaporated to dryness to provide the product (430 mg) in 53% yield.

IX. Synthesis of Dihydro-7-benzylthio-2-pyrindine-7-carboxylic acid, methyl ester To the methyl ester (4.3 mmol) in anhydrous THF (125 ml) at −78° C. is added n-BuLi (4.51 mmol, 2.2M in hexanes). The reaction mixture is stirred at −78° C. for 30 minutes and then to this added benzyldisulfide (6.45 mmol) in THF (15 ml). The mixture is stirred an additional 2 hours at −78° C. then at room temperature overnight. The reaction is quenched by the addition of saturated aqueous ammonium chloride. The layers are separated and the aqueous layer is extracted with methylene chloride. The organic layers are combined, dried over sodium sulfate, filtered and concentrated under reduced pressure. The desired product is isolated cleanly by flash chromatography with 2% iospropanol in methylene chloride on silica gel.

X. Synthesis of Dihydro-7-benzylthio-2-pyrindine-7-carboxylic acid, HCl salt

Dihydro-7-benzylthio-2-pyrindine-7-carboxylic acid, methyl ester (0.53 g, 3.0 mmol) is heated at 58° C. in 1N NaOH (3.1 ml) and methanol (30 ml) for 2.5 hours. The solution is evaporated to dryness under vacuum and the resulting residue is stirred in ethanolic-HCl to precipitate the product. The desired product is collected by filtration.

XI. Synthesis of [1-hydroxy-(dihydro-7-benzylthio-2-pyrind-7-yl)methylene]bis[phosphonic acid]

To phosphorus trichloride (1.19 g, 8.63 mmol) is added a slurry of dihydro-2-pyrindine-7-carboxylic acid, HCl salt (0.54 g, 2.88 mmol), phosphorous acid (708 mg, 8.63 mmol) and chlorobenzene (10 ml). The reaction mixture is stirred and heated at 105° C. for 4 hours. The mixture is then cooled to room temperature and the chlorobenzene is decanted off. To the crude residue is added 1N HCl (10 ml) and the mixture is heated at reflux overnight. The reaction mixture is then concentrated under reduced pressure and triturated in acetone to provide the desired product (107 mg) in good purity.

XII. Synthesis of [1-hydroxy-(dihydro-7-mercapto-2-pyrind-7-yl)methylene]bis[phosphonic acid]

The benzyl sulfide (0.25 mmol) is added to freshly distilled ammonia (125 ml) at −78° C. Small pieces of sodium metal are added and the blue color is maintained for 20 minutes. The reaction mixture is then quenched by the addition of isobutylene and the ammonia is allowed to evaporate. The crude residue is dissolved in a minimum amount of water and the desired thiol is precipitated by the addition of isopropanol.

EXAMPLE N

Synthesis of [Octahydro-4-(2-mercaptoethyl)-pyrrolo[3,2-b]pyridin-2-yl]bis[phosphonic acid]

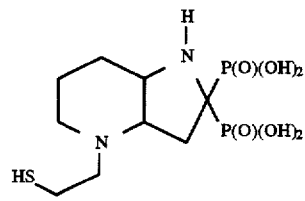

I. Synthesis of 1,3-dihydro-4-(2-acetylthioethyl)-2-oxo-2H-pyrrolo[3,2-b]pyridinium bromide To 1,3-dihydro-2H-pyrrolo[3,2-b]pyridin-2-one (6.25 g, 0.05 mol) [prepared as described in J. Org. Chem. Vol.37, pp. 51–4, 1972] in acetonitrile (500 ml) is added S-acetyl-2-bromoethanethiol. The reaction mixture is heated at reflux for 12 hours under an atmosphere of nitrogen. The reaction mixture is the concentrated under reduced pressure and the crude residue is triturated in diethyl ether, the product can be further purified by flash chromatography with 5% isopropanol in methylene chloride on silica gel.

II. Synthesis of 1,3-dihydro-4-(2-mercaptoethyl)-2,2-diphosphono-2H-pyrrolo[3,2-b]pyridinium chloride 1,3-Dihydro-4-(2-acetylthioethyl)-2-oxo-2H-pyrrolo[3,2-b]pyridiniumbromide is treated with phosphorous acid (7.7 g) in chlorobenzene (28 ml) and heated to 110° C. To the rapidly stirring mixture is added phosphorus trichloride (9.0 ml) and the heating is continued for 5 hours. After cooling to ambient temperature the solvent is decanted and aqueous HCl (28 ml, 1M) is added. The mixture is heated at reflux for an additional 12 hours. The reaction mixture is cooled and concentrated to dryness. After triturating the residue with several portions of acetone, the bisphosphonic acid is obtained in a pure state.

III. Synthesis of [octahydro-4-(2-mercaptoethyl)-2H-pyrrolo[3,2-b]pyridin-2-ylidene]bis[phosphonic acid]

Using essentially the same hydrogenation procedure as described in Example B hereinbefore, 1,3-dihydro-4-(2-mercaptoethyl)-2,2-diphosphono-2H-pyrrolo[3,2-b]pyridinium chloride is converted to [octahydro-4-(2-mercaptoethyl)-2H-pyrrolo[3,2-b]pyridin-2-ylidene]bis[phosphonic acid].

EXAMPLE O

Synthesis of (3-acetylthio)-cyclopentane-1,1-bisphosphonic acid

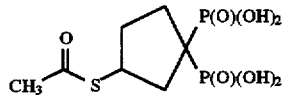

I. Synthesis of 3-cyclopentene-11-bisphosphonic acid tetra isopropyl ester

To potassium hydride (2.29 g, 0.02 mol) in toluene (30 ml) at 0° C. is slowly added tetra isopropyl methylene bisphosphonate (3.4 g, 0.01 mol) in toluene (12 ml). The reaction mixture is allowed to warm to room temperature and stirred for 1 hour. The reaction is then re-cooled to 0° C.

and to this is added cis-1,4-dichlorobutene (1.5 g, 0.012 mol) in toluene (6 ml). The reaction mixture is heated at 90° C. for 6 hours. The reaction is cooled and then washed with saturated aqueous ammonium chloride. The organic layer is dried over sodium sulfate, filtered and then concentrated under reduced pressure. The cyclopentene adduct is obtained as a colorless oil by flash chromatography on silica gel (5% isopropanol in ethyl acetate).

II. Synthesis of 3-cyclopentene-1,1-bisphosphonic acid

The tetra isopropyl ester (1 g) is heated at 100° C. in concentrated HCl for 12 hours under an atmosphere of nitrogen. The reaction mixture is then cooled and concentrated to dryness. The crude residue is washed with isopropyl alcohol followed by acetone. The product is obtained as a white solid by recrystallization from water and ethanol.

III. Synthesis of (3-acetylthio)-cyclopentane-1,1-bisphosphonic acid

A solution of a the bisphosphonic acid (0.31 g, 1.3 mmol) and thiol acetic acid (0.24 ml, 3.25 mmol) in water (5 ml) is irradiated with a 250 W ultraviolet sunlamp for 12 hours. The reaction mixture is concentrated and the product is obtained by recrystallization from water and ethanol.

EXAMPLE P

Schenk Model

The compounds are evaluated for in vivo bone resorption inhibition and mineralization inhibition in an animal model system known in the field of bone metabolism as the Schenk Model. The general principles of this model system are disclosed in Shinoda et al., Calcif. Tissue Int., 35, 87–99 (1983); and in Schenk et al., Calcif. Tissue Res. 11, 196–214 (1973), the disclosures of which are incorporated herein by reference.

Materials and Methods

Animals

Preweaning 17-day-old (30 gms) male Sprague Dawley rats (Charles River Breeding Laboratories) are shipped with their mothers and placed in plastic cages with their mothers upon arrival. At 19 days of age, pups receiving Rat Chow and water ad libitum are randomly allocated into treatment or control groups comprising seven animals per group. On day 1 and again on day 7 all animals are given an intraperitoneal ("IP") injection of Calcein (1% solution in 0.9% saline solution; dosed at 0.2 ml/100 g body weight). On day 4 all animals are given an IP injection of tetracycline hydrochloride (1% solution in 0.9% saline solution; dosed at 0.2 ml/100 g body weight). These compounds label actively mineralizing bone and cartilage.

Dose Solutions and Dosing Procedure

All solutions are prepared for subcutaneous injection in 0.9% normal saline and adjusted to pH 7.4 using NAOH and/or HCl. Dose solution calculation is made by considering the mass of powder (based on molecular weight, hydration) of the active material in mg/kg (body weight) that corresponds to mgp/kg. Concentrations are based on dosing 0.2 ml/100 g body weight. Typically, all compounds are administered at 0.01, 0.1, 1.0 and 10.0 mg P/kg/day for 7 days. Compounds showing activity at 0.1 mg P/kg/day are then tested at logarithmic decrements down to 0.001 mg P/kg/day. Adjustments in dosage based on changes in body weight are made on a daily basis.

Necropsy, Tissue Processing and Histomorphometry

On day 8 after the start of dosing, all animals are sacrificed by IP overdose of pentabarbitol. Tibias are dissected free and placed in 70% ethyl alcohol. One tibia is dehydrated in graded ethanol solutions and embedded in methyl methacrylate as described in Schenk, Methods of Calcified Tissue Preparation (G. R. Dickson, Editor; Elsevier Science Publ., The Netherlands; 1984), the disclosures of which are incorporated herein by reference in their entirety. The tibia is sectioned longitudinally through the metaphyseal area. Specimens are stained on one surface with silver nitrate and mounted on microscope slides for evaluation with a Quantimet Image Analyzer (Cambridge Instruments, Inc.) using both incandescent and ultraviolet illumination. Metaphyseal trabecular bone content is measured in the region between the fluorescent label and the growth plate: expressed as percent of total area (bone+ marrow). Epiphyseal growth plate width is obtained as the mean value of 10 equally-spaced measurements across the section.

Statistical evaluation of data is made using parametric and non-parametric analysis of variance and Wilcoxons rank sum test to determine a statistically significant effect compared to control animals. The Schenk model provides data for in vivo bone resorption inhibition by the compounds.

EXAMPLE O

Adjuvant Arthritis Model

There are numerous animal models of arthritis, among these is adjuvant-induced arthritis using Mycobacterium butyricum. This model in a number of ways mimics rheumatoid arthritis in the human (joint swelling associated with cellular and pannus invasion of the joint space, bone resorption, and release of chemotaxic factors and lysosomal constituents into the joint space) (1,2). A number of prophylactic and therapeutic studies have indicated the potential use of anti-inflammatory drugs (3,4) and diphosphonates in arthritis (5,6).

REFERENCES

1. Pearson, C., Wood F. (1959), Studies of Polyarthritis and Other Lesions Induced by Injection of Mycobacterial Adjuvant. 1. General Clinical and Pathological Characteristics and Some Modifying Factors, Arth. Rheum., 2:440–459.
2. Blackman, A., Burns, J. W., Framer, J. B., Radziwonik, H., Westwick, J. (1977), An X-ray Analysis of Adjuvant Arthritis in the Rat. The Effect of Prednisolone and Indomethacin, Agents and Actions, 7:145–151.
3. Winter, C. A., Nuss, G. W. (1966), Treatment of Adjuvant Arthritis in Rats with Anti-inflammatory Drugs, Arth. Rheum., 9:394–404.
4. Winder, C. V., Lembke, L. A., Stephens, M. D. (1969), Comparative Bioassay of Drugs in Adjuvant-Induced Arthritis in Rats: Flufenamic Acid, Mefenamic Acid, and Phenylbutazone, Arth. Rheum., 12:472–482.
5. Francis, M. D., Flora, L. King, W. R. (1972), The Effects of Disodium Ethane-1-Hydroxy-1-Diphosphonate on Adjuvant Induced Arthritis in Rats, Calcif. Tiss. Res., 9:109–121.
6. Flora, L. (1979), Comparative Antiinflammatory and Bone Protective Effects of Two Diphosphonates in Adjuvant Arthritis, Arth. Rheum, 22:340–346.

Adjuvant arthritis is a severe cellulitis and synovitis induced in male rats (either Sprague Dawley or Lewis strain) by a single subcutaneous (SC) injection of Mycobacterium butyricum (8 mg/ml) in mineral oil on day 0. The compounds are dosed once daily either orally (PO) or parenterally (SC) and can be tested in either prophylactic (from day 0) or therapeutic (from day 9 or 10 or 14) protocols. Antiarthritic efficacy can be measured as a reduction in paw volume, body weight loss, bone loss or reactive new bone formation compared to the saline-treated arthritic controls. Treatment can be stopped and the "flare" response (rapid increase in inflammation) examined, which indicates a compound's ability to maintain efficacy.

Materials and Methods

A. Animals

Animals used are male Lewis rats (LEW). On arrival, the rats are randomized by computer generated random numbers and placed in individual wire suspended cages. Food and water are administered ad libitum, throughout the entire study. Routine care and maintenance of the animals are performed according to State and Federal regulations. Each rat is identified with a number placed in front of the cage and on the tail of the rat.

B. Experimental Design

On day 1 body weights (BW) and hind paw volume [(PV) recorded by a mercury displacement method using a pressure transducer linked into a computer] measurements are taken on all rats. On day 0, the induction of arthritis using MFA [*Mycobacterium butyricum* (Mb) 4.4 mg/kg in oil] is as follows: rats are anesthetized and receive a single SC injection of MFA at the base of the tail under aseptic conditions.

Paw volumes and body weights are measured thereafter on various days, usually twice a week. For the prophylactic protocol, rats are randomly allocated into groups of 8–10 rats and treatment begins on day 0 and continues daily until termination. For the therapeutic protocol, the rats are randomized into treatment groups of 8–10 rats according to their PV on day 10. Dosing begins on day 10 and continues daily until termination. For both protocols, animals are placed in shoe box cages with deep bedding on or before day 10.

Dosing Solutions

Drugs are weighed out on a calibrated balance and then mixed with deoxygenated water in a volumetric flask. The stock solution is filtered through a 0.45 μm sterile filter into a sterile storage container. When not in use, the stock solution is kept refrigerated.

On a daily basis, a specific amount of solution is removed from the stock solution, put into small dosing beaker and then adjusted to pH 7.4 according to a predetermined calculation. Further dilutions of the adjusted solution can be made if necessary (with deoxygenated water).

Drug calculations are made based on the molecular weight, the purity of the compound, the amount based on mg/kg (body weight) and the desired final concentration in mgP/kg. The volume dosed per rat is 0.1 ml/100 gm of body weight subcutaneously, given as an injection in the inguinal fold of the animal, alternating sides each day or 1 ml/200 gm BW given orally using a curved stainless steel dosing tube. Adjustments based on changes in body weight are made weekly.

Radiographs, Necropsy and Tissue Collection

At termination, each rat is sacrificed with 1 ml Socomb® intraperitoneally (IP). Immediately a whole body radiograph is taken by a Torrox 120D x-ray unit at MA=5, ISUP=50 and time=60 seconds on Kodak non-screen medical film. Hind legs are removed from each rat and fixed in 10% buffered formalin along with a piece of liver, kidney, spleen, and thimus. The tibiotarsal joints are decalcified in 4% EDTA, pH 7.4 and processed routinely in paraffin blocks and H+E stain. The organ parts also processed in paraffin and stained H+E.

The histology sections are evaluated qualitatively for bone and soft tissue lesions using light microscopy. Radiographs are graded for bone resorption (BR) in 6 anatomical trabecular bone sites in each hind leg and 4 sites in each front leg on a scale of 0–3 giving an arbitrary score of 0–60 for all 4 legs. For reactive new bone formation (RNB), radiographs are graded on a severity scale of 0–3 for the lateral and medical surfaces of the tibia and then 0–2 for all other areas mentioned above, giving an arbitrary score of 0–44.

D. Statistical Analysis

Data analysis on paw volume, bone resorption and reactive new bone formation is performed by student's t-test and one-way analysis of variance with Tukeys (SAS) (12). Differences are considered significant at p=0.05 or less.

This model provides in vivo data for the efficacy of antiarthritic compounds in terms of reducing paw swelling bone loss and reactive new bone formation compared to the saline treated arthritic animals.

EXAMPLE R

Capsules are prepared having the following composition:

|  | Mg Per Capsule |
|---|---|
| Active Ingredient | |
| Cis-octahydro-7-(2-mercaptoethyl)-1-pyrindine-6,6-DP | 350.0 |
| Excipients | |
| Lactose | 90.0 |
| Microcrystalline Cellulose | 60.0 |
| Magnesium Stearate | 1.0 |

The capsules having the above composition are prepared using conventional methods as described below:

The active ingredient is mixed with the microcrystalline cellulose in a turn shell blender for approximately ten (10) minutes.

The resulting mixture is passed through a hammer mill with an 80 mesh screen.

The mixture is put back into the twin shell blender along with the lactose and is then mixed for approximately fifteen (15) minutes.

The magnesium stearate is next added and blended for an additional five (5) minutes. The resulting blend is then compressed on a piston-activated capsule filler.

The above capsules are administered orally twice daily for 6 months substantially reduce bone resorption in a patient weighing approximately 70 kilograms afflicted with osteoporosis. Similar results are obtained when cis-octahydro-7-(2-mercaptoethyl)-1-pyrindine-6,6-DP in the above described capsules is replaced with octahydro-7-(2-mercaptoethyl)-2-pyrindine-6,6-DP; or N-methyl-octahydro-7-(2-mercaptoethyl)-1-pyrindine-6,6-DP; or a pharmaceutically acceptable salt or ester of these diphosphonate compounds.

EXAMPLE S

Tablets are prepared by conventional methods, formulated as follows:

|  | Mg per tablet |
|---|---|
| Active Ingredient | |
| Cis-octahydro-7-(2-mercaptoethyl)-1-pyrindine-6,6-DP | 700.0 |
| Excipients | |
| Lactose (spray-dried) | 200.0 |
| Starch (1500) | 100.0 |
| Magnesium Stearate | 25.0 |

Tablets are prepared having the above composition using conventional methods as described below:

The active ingredient is ground in a ball mill for approximately thirty (30) minutes. The milled active ingredient is then blended in a twinblade mixer with the spray-dried lactose for approximately twenty (20) minutes.

The starch is added to the mixture and is then mixed for an additional fifteen (15) minutes. The blend is compressed into tablets on a standard tablet press.

The above tablets administered orally twice daily for 6 months substantially reduce bone resorption in a patient weighing approximately 70 kilograms afflicted with Paget's disease. Similar results are obtained when octahydro-3-mercapto-1-pyrindine-6,6-DP in the above described tablets is replaced with octahydro-3-(3-mercaptopropyl-1-pyrindine-6,6-DP; octahydro-3-(4-mercaptobutyl-1-pyrindine-6,6-DP; octahydro-3-mercapto-1-pyrindine-7,7-DP; octahydro-1-pyrindine-5,5-DP; or N-methyl-octahydro-7-(2-mercaptoethyl)-1-pyrindine-6,6-DP; or a pharmaceutically acceptable salt or ester of these diphosphonate compounds.

EXAMPLE T

Injectable solutions are prepared by conventional methods using 10.0 ml of physiological saline solution and 7.0 mg P of cis-octahydro-7-(2-mercaptoethyl)-1-pyrindine-6,6-DP, adjusted to pH=7.4.

One injection, one time daily for 4 days, results in appreciable alleviation of hypercalcemia of malignancy in patients weighing approximately 70 kilograms.

EXAMPLE U

A Caucasian male, weighing approximately 92 kilograms, seventy-two years of age, suffering from moderate to severe pain, and occasional swelling, of the right knee. After approximately one year of steadily increasing discomfort, he visits a physician who renders a clinical diagnosis of osteoarthritis of the right knee, which was subsequently verified by X-ray diagnosis.

After a period of ameliorative therapy of various NSAIDs, including aspirin, naprosen, and ketoprofen, his symptoms continue to worsen and his condition appears to degenerate. He returns to his physician who then prescribes the tablets prepared as described in Example S twice daily two hours before or after meals for a period of three months. His clinical symptoms of pain and swelling, particularly with extended walking, improved significantly after his 3 months of therapy. At the conclusion of three months at a dosage of 1 capsules prepared as described in Example R per day, the therapy is continued at one-half the dosage originally prescribed (i.e. 1 capsule per day) indefinitely.

EXAMPLE V

A black female, weighing approximately 65 kilograms, fifty-five years of age, presents with swelling and deformation of the finger joints of both hands, with partial loss of strength and/or dexterity of her fingers and hands. Upon visual and X-ray examination and various appropriate clinical tests approved by the American Rheumatological Association (ARA) she is diagnosed with rheumatoid arthritis.

After an unsuccessful analgesic and anti-inflammatory therapy, her physician prescribes the capsules prepared in Example R, two times daily two hours before or after meals for a period of four months. After a month of therapy, her symptoms of knuckle swelling noticeably improves and her range of finger motion increases significantly; she continues therapy for the remainder of the four months, after which her physician continues the prescribed dose for an additional two months.

EXAMPLE W

A female of Hispanic origin, twelve years of age, weighing approximately 37 kilograms, presents to the physician with idiopathic juvenile rheumatoid arthritis. Her symptoms include marked inflammation of multiple joints, complicated by heat and tenderness and indicating rapid and pathological degeneration of joint function.

Her physician refers her to a rheumatologist who immediately prescribes aggressive therapy by IV administration of the solution prepared as described in Example T over a period of three days, at the rate of 1 injection per day, administered over two hours. At the conclusion of the IV regimen, the physician prescribes the two tablets prepared as described in Example R, twice a day, two hours before and after meals, for a period of two months, during which she exhibits marked improvement with increased mobility and decreased pain. For the succeeding two months, the physician reduces her dose to ¾ of the original oral dose by prescribing 3 tablets over a period of two days, i.e. one 2-tablet day alternating with one 1-tablet day. At the conclusion of this regimen the dosage is again reduced to ¼ of the original oral dose by giving her the capsules prepared as described in Example R, 1 capsule every day for an additional four months.

What is claimed is:

1. Cyclic thio-substituted phosphonates, and the pharmaceutically-acceptable salts and esters thereof, having the following structure:

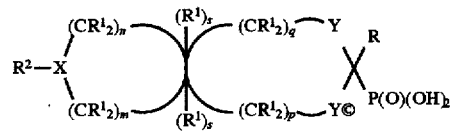

wherein (a) X and Y are independently selected from nil, oxygen, sulfur, or nitrogen, (b) R is $PO_3H_2$ or $P(O)(OH)R^4$, wherein $R^4$ is substituted or unsubstituted $C_1$–$C_8$ alkyl;

(c) m and n are integers from 0 to 5, and m+n equals 0 to 5;

(d) p and q are integers from 0 to 3, and p+q equals 1 to 3;

(e) s is an integer from 0 to 2 and when X is nil and m+n 0, s=2;

(f) each $R_1$ is independently selected from —$SR^6$; $R^8SR^6$; nil; hydrogen; unsubstituted or substituted $C_1$–$C_8$ alkyl; unsubstituted or substituted aryl; hydroxy; amido; alkoxy; —$CO_2R^3$; —$O_2CR^3$; —$NR^3_2$; —$N(R^3)C(O)$ R$^3$; —OR$^3$; —C(O)N(R$^3$)$_2$; substituted or unsubstituted benzyl; nitro; and combinations thereof;

(g) R$^2$ is one or more substituents of X and Y and is independently selected from the group consisting of —SR$^6$; R$^8$SR$^6$; nil; hydrogen; unsubstituted or substituted C$_1$–C$_8$ alkyl; unsubstituted or substituted aryl; hydroxy; amido; —CO$_2$R$^3$; —O$_2$CR$^3$; —N(R$^3$)C(O)R$^3$; —OR$_3$; —N(R$^3$)$_2$; —C(O)N(R$^3$)$_2$; substituted or unsubstituted benzyl; nitro; or combinations thereof;

(h) R$^3$ is independently selected from hydrogen; substituted or unsubstituted C$_1$–C$_8$ alkyl; or R$^8$SR$^6$;

(i) R$^6$ is H; —C(O)R$^7$; —C(S)R$^7$; C(O)N(R$^7$)$_2$; C(S)N(R$^7$)$_2$; C(O)OR$^7$, or C(S)OR$^7$; wherein R$^7$ is hydrogen, or substituted or unsubstituted C$_1$–C$_8$ alkyl;

(j) R$^8$ is substituted or unsubstituted C$_1$–C$_8$ alkyl;

(k) wherein any ring formed is of 4 to 7 members;

provided that at least one of R$^1$, R$^2$, and R$^3$ is SR$^6$ or R$^8$SR$^6$.

2. A compound according to claim 1, of formula:

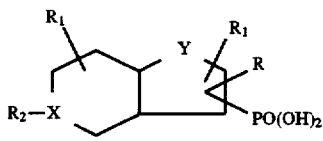

wherein the ring system is singly or multiply saturated or unsaturated;

X is nitrogen;

Y is CH$_2$ or NH;

R is geminal to the PO(OH)$_2$ and is SO$_3$H, COOH, PO(OH)R$_4$; and R$_4$ is a substituted or unsubstituted C$_1$ to C$_8$ alkyl;

R$_1$ is independently chosen from the group consisting of hydrogen, alkyl, thioalkyl, and alkyl thioalkyl;

R$_2$ is independently chosen from the group consisting of hydrogen, alkyl thio, thio alkyl, alkyl thioalkyl, alkoxy, hydroxy, amino, alkyl amino and dialkyl amino.

3. A compound according to claim 1, of formula:

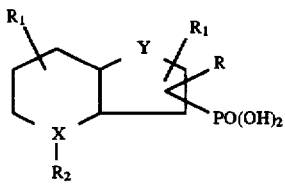

wherein the ring system is saturated or singly or multiply unsaturated;

X is nitrogen;

Y is CH$_2$ or NH;

R is geminal to the PO(OH)$_2$ and is chosen from the group consisting of SO$_3$H, COOH, PO(OH)R$_4$; and R$_4$ is a substituted or unsubstituted C$_1$ to C$_8$ alkyl;

R$_1$ is independently chosen from the group consisting of hydrogen, alkyl, thioalkyl, and alkyl thioalkyl;

R$_2$ is independently chosen from the group consisting of hydrogen, alkyl thio, thio alkyl, alkyl thioalkyl, alkoxy, hydroxy, amino, alkyl amino and dialkyl amino.

4. A compound according to claim 1, of formula:

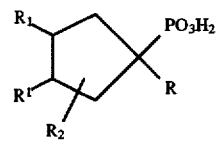

wherein the ring system is saturated or singly or multiply unsaturated to any degree;

R is PO$_3$H$_2$, PO(OH)R$_4$; wherein R$_4$ is a substituted or unsubstituted C$_1$ to C$_8$ alkyl;

R$_1$ is independently chosen from the group consisting of SR$_6$, R$_8$SR$_6$, hydrogen, alkyl, alkoxy hydrogen, amino, alkyl amino, dialkyl amino, amido, alkoxy carbonyl and alkenoyloxy;

R$_2$ is independently chosen from the group consisting of SR$_6$, R$_8$SR$_6$, hydrogen, alkyl, alkoxy hydrogen, amino, alkyl amino, dialkyl amino, amido, alkoxy carbonyl and alkenoyloxy.

5. A compound of formula:

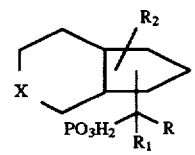

wherein the ring system is saturated or singly or multiply unsaturated;

X is nitrogen;

R is PO$_3$H$_2$, PO(OH)R$_4$ and R$_4$ is a substituted or unsubstituted C$_1$ to C$_8$ alkyl;

R$_1$ is SR$_6$, R$_4$SR$_6$, hydrogen, alkyl, alkoxy hydrogen, amino, alkyl amino, dialkyl amino, amido, alkoxy carbonyl or alkenoyloxy;

R$_2$ is SR$_6$, R$_4$SR$_6$, hydrogen, alkyl, alkoxy hydrogen, amino, alkyl amino, dialkyl amino, amido, alkoxy carbonyl or alkenoyloxy;

R$_6$ is H, COR$_7$, CSR$_7$, CON(R$_7$)$_2$, CSN(R$_7$)$_2$, COOR$_7$, CSOR$_7$; wherein R$_7$ is independently hydrogen or R$_4$.

6. The compound of claim 1, wherein said compound is selected from the group consisting of:

Dihydro-7-Mercapto-1-pyrindine6,6-bisphosphonic acid;

Octahydro-7-Mercapto-1-pyrindine6,6-bisphosphonic acid;

Dihydro-7-(2-mercaptoethyl)-1-pyrindine-6,6-bisphosphonic acid;

Octahydro-7-(2-mercaptoethyl)-1-pyrindine-6,6-bisphosphonic acid;

Dihydro-3-mercapto-1-pyrindine-6,6-bisphosphonic acid;

Octahydro-3-mercapto-1-pyrindine-6,6-bisphosphonic acid;

Dihydro-4-mercapto-2-pyrindine-6,6-bisphosphonic acid;

Octahydro-4-mercapto-2-pyrindine-6,6-bisphosphonic acid;

Dihydro-3-(4-mercaptobutyl)-1-pyrindine-6,6-bisphosphonic acid;

Octahydro-3-(4-mercaptobutyl)-1-pyrindine-6,6-bisphosphonic acid;

Dihydro-4-(4-mercaptobutyl)-2-pyrindine-6,6-bisphosphonic acid;

Octahydro-4-(4-mercaptobutyl)-2-pyrindine-6,6-bisphosphonic acid;

[1-hydroxy-(dihydro-7-mercapto-2-pyrind-7-yl)methylene]bis[phosphonic acid];

[Octahydro-4-(2-mercaptoethyl)-pyrrolo[3,2-b]pyridin-2-yl]bis[phosphonic acid]; and (3-acetylthio)-cyclopentane-1,1-bisphosphonic acid.

* * * * *